United States Patent [19]

Grotendorst et al.

[11] Patent Number: 5,849,534
[45] Date of Patent: Dec. 15, 1998

[54] DNA ENCODING LEUKOCYTE DERIVED GROWTH FACTOR-2 (LDGF-2)

[75] Inventors: Gary R. Grotendorst, Miami; Naoko Iida, Miami Beach, both of Fla.

[73] Assignee: University of South Florida, Tampa, Fla.

[21] Appl. No.: 465,095

[22] Filed: Jun. 5, 1995

Related U.S. Application Data

[60] Division of Ser. No. 179,656, Jan. 7, 1994, which is a continuation-in-part of Ser. No. 1,177, Jan. 7, 1993, abandoned, which is a continuation-in-part of Ser. No. 472,377, Feb. 1, 1990, abandoned.

[51] Int. Cl.$^6$ .......................... C07K 14/475; C12N 5/10; C12N 1/21; C12N 15/12
[52] U.S. Cl. .................... 435/69.4; 435/172.3; 435/69.6; 435/69.1; 530/399; 530/350; 536/23.5; 536/24.1
[58] Field of Search ................................. 536/23.5, 24.1; 435/172.3, 69.1, 69.6, 69.4; 530/399, 350

[56] References Cited

FOREIGN PATENT DOCUMENTS

WO 85/01067  3/1985  WIPO.
WO 90/06321  6/1990  WIPO.

OTHER PUBLICATIONS

*Abstracts, 20th Annual Meetings, Journal of Cellular Biochemistry, Keystone Symposia on Molecular & Cellular Biology*, pp. 159, 162, 164, 169, 171, 191 and 197 (1991).
Carrico et al., "Biology of Wound Healing," *Surgical Clinics of North America*, vol. 64, No. 4, pp. 721–733 (1984);.
Ford et al., "Characterization of Wound Cytokines in the Sponge Matrix Model," *Arch Surg*, vol. 124, 1422–1428 (1989);.
Grotendorst, et al., "Differentiation Production of a Platelet–Derived Growth Factor–Like Mitoattractant by Endoderm Cells Derived from Embryonal Carcinoma Cells," *Journal of Cellular Physiology*, vol. 134, pp. 437–444 (1988);.
Jose et al., "Identification of a second neutrophil–chemoattractant cytokine generated during an inflammatory reaction in the rabbit peritoneal cavity in vivo," *Biochem. J.*, vol. 278, pp. 493–497 (1991);.
Kapp and Zeck–Kapp, "Activation of the oxidative metabolism in human polymorphonuclear neutrophilic granulocytes: The role of immuno–modulating cytokines," Abstract, 7996000, EMBASE No. 91028645;.
Matsuoka and Grotendorst, "Two peptides related to platelet–derived growth factor are present in human wound fluid," *Proc. Natl. Acad. Sci. USA*, vol. 86, pp. 4416–4420 (1989);.
Pencev and Grotendorst, "Human Peripheral Blood Monocytes Secrete a Unique Form of PDGF," *Oncogene Research*, vol. 3, No. 4, pp. 333–342 (1988);.

Schröder et al., "Identification of a novel platelet–derived neutrophil–chemotactic polypeptide with structural homology to platelet–factor 4," *Biochemical and Biophysical Research Communications*, vol. 172, No. 2, pp. 898–904 (1990);.
Schröder et al., "IL–1α or tumor necrosis factor–α stimulate release of three NAP–1/IL–8–related neutrophil chemotactic proteins in human dermal fibroblasts," *The Journal of Immunology*, vol. 144, No. 6, pp. 2223–2232 (1990);.
Schröder et al., "Lipopolysaccharide–stimulated human monocytes secrete, apart from neutrophil–activating peptide 1/interleukin 8, a second neutrophil–activating protein," *J. Exp. Med.*, vol. 171, pp. 1091–1100 (1990).
ten Dijke and Iwata, "Growth Factors for Wound Healing," *Bio/Technology*, vol. 7, pp. 793–798 (1989).
Van Brunt, "Lessons from Wound–healing Clinical Trials," *Bio/Technology*, vol. 7, pp. 15–16 (1989).
Walz et al., "A Novel Cleavage Product of B–Thromboglobulin Formed in Cultures of Stimulated Mononuclear Cells Activates Human Neutrophils" *Biochemical and Biophysical Research Communication*, vol. 159, No. 3 pp. 969–975 (1989).
Walz et al., "Effects of the Neutrophil–Activating Peptide NAP–2, Platelet Basic Protein, Connectiv Tissue–Activating Peptide III, and Platelet Factor 4 on Human Neutrophils" *Journal Experimental Medicine*, vol. 170, pp. 1745–1750 (1989);.
Walz et al., "Structure and Neutrophil–activating Properties of a Novel Inflammatory Peptide (ENA–78) with Homology to Interleukin 8," *J. Exp. Med.*, vol. 174, pp. 1355–1362 (1991);.
Wenger et al., "Cloning of cDNA Coding for Connective Tissue Activating Peptide III From a Human Platelet–Derived λgtII Expression Library," *Blood*, vol. 73, No. 6, pp. 1498–1503 (1989);.
"Wound Healing Flow Chart" (cited by the Examiner Dec., 1992 in parent application, Ser. No. 07/472,377).
Pilbeam et al. 1993. Bone 14:717–20.
Bowie et al. 1990. Science 247: 1306–1310.
Ngo et al. 1994. The Protein Folding Problem & Tertiary Structure Prediction, Merz et al, eds., Birkhauser, Boston, pp. 491–495.

*Primary Examiner*—Elizabeth C. Kemmerer
*Attorney, Agent, or Firm*—Lahive & Cockfield, LLP; Giulio A. DeConti, Jr.; Elizabeth A. Hanley

[57] ABSTRACT

A protein, Leukocyte Derived Growth Factor 2 (hereinafter LDGF2) having PDGF-like activity is described. LDGF2 reacts with PDGF receptors and possesses mitogenic and/or chemotactic activity for various cell types, particularly connective tissue cells. LDGF2 may be used as the active ingredient in therapeutic compositions, e.g. wound healing compositions, or even further may be used as an additive to cell culture media for the purpose of stimulating cell growth. The protein has a molecular weight of about 7000 daltons determined by SDS gel electrophoresis and is about 61 amino acids in length.

24 Claims, 18 Drawing Sheets

| | | | |
|---|---|---|---|
| LDGF2 | | TC | 2 |
| | | ** | |
| LDGF1 | GCAACTCACCCTCACTCAGAGGTCTTCTGGTTCTGGAAACAACTCTAGCTCAGCCTTCTC | | 60 |
| LDGF2 | CACCATGAGCCTCAGACTTGATACCACCCCTTCCTGTAACAGTGCGAGACCACTTCATGC | | 62 |
| | ************************************************************ | | |
| LDGF1 | CACCATGAGCCTCAGACTTGATACCACCCCTTCCTGTAACAGTGCGAGACCACTTCATGC | | 120 |
| LDGF2 | CTTGCAGGTGCTGCTGCTTCTGTCATTGCTGCTGACTGCTCTGGCTTCCTCCACCAAAGG | | 122 |
| | ************************************************************ | | |
| LDGF1 | CTTGCAGGTGCTGCTGCTTCTGTCATTGCTGCTGACTGCTCTGGCTTCCTCCACCAAAGG | | 180 |
| LDGF2 | ACAAACTAAGAGAAACTTGGCGAAAGGCAAAGGTCACATTTTCTACCCTAGAGGAAAGTC | | 182 |
| | ****************************** ******** | | |
| LDGF1 | ACAAACTAAGAGAAACTTGGCGAAAGGCAAAG----------------AGGAAAGTC | | 221 |
| LDGF2 | TAGACAGTGACTTGTATGCTGAACTCCGCTGCATGTGTATAAAGACAACCTCTGGAATTC | | 242 |
| | ************************************************************ | | |
| LDGF1 | TAGACAGTGACTTGTATGCTGAACTCCGCTGCATGTGTATAAAGACAACCTCTGGAATTC | | 281 |
| LDGF2 | ATCCCAAAAACATCCAAAGTTTGGAAGTGATCGGGAAAGGAACCCATTGCAACCAAGTCG | | 302 |
| | ************************************************************ | | |
| LDGF1 | ATCCCAAAAACATCCAAAGTTTGGAAGTGATCGGGAAAGGAACCCATTGCAACCAAGTCG | | 341 |
| LDGF2 | AAGTGATAGCCACACTGAAGGATGGGAGGAAAATCTGCCTGGACCCAGATGCTCCCAGAA | | 362 |
| | ************************************************************ | | |
| LDGF1 | AAGTGATAGCCACACTGAAGGATGGGAGGAAAATCTGCCTGGACCCAGATGCTCCCAGAA | | 401 |
| LDGF2 | TCAAGAAAATTGTACAGAAAAAATTGGCAGCTGAAGCTGAAGAAGATGGGGACCTGCAGT | | 422 |
| | ***************************** *** *   *  ***    *  *  ** | | |
| LDGF1 | TCAAGAAAATTGTACAGAAAAAATTGGCAGGTGATGAATCTGCTGATTAATTTGTTCTGT | | 461 |
| LDGF2 | GCCTGTGTGTGAAGACCACCTCCCAGGTCCGTCCCAGGCACATCACCAGCCTGG--AGGT | | 480 |
| | ***   * ********   *   *    ***    *           * | | |
| LDGF1 | TTCTGCCAAACTTCTTTAACTCCCAGGAAGGGTAGAATTTTGAAACCTTGATTTTCTAGA | | 521 |
| LDGF2 | GATCAAGGCCGGACCCCACTGCCCCACTGCCCAACTGATAGCCACGCTGAAGAATGGAAG | | 540 |
| | * **     *    *   *   *  **  *    * ***      **    ** | | |
| LDGF1 | GTTCTCATTTATTCAGGATACCTATTCTTACTGTATTAAAATTT---GGATATGTGTTTC | | 578 |
| LDGF2 | GAAAATTTGCTTGGACCTGCAAGCCCCGCTGTACAAGAAAATAATTAAGA-AACTTTTGG | | 599 |
| | *  *   * *  **      ***    ***        ****   *      * | | |
| LDGF1 | ATTCTGTCTCAAAAATCA-CATTTTATTCTGAGGAAGGTTGGTTAAAAGATGGCAGAAAG | | 637 |
| LDGF2 | AGAGTTAGCTACTAGCTGCCTACGTGTGTGCATTTGCTATATAGCATACTTCTTTTTTCC | | 659 |
| | *  *  *    *  ****    *  * **     *       *   *          ** | | |
| LDGF1 | AAGATGAAAATAAATAAGCCT----GGTTTCAA---C-------C---CC-------TC | | 672 |
| LDGF2 | AGTTTCAATCTAACTGTGAAAGAACTTCTGATATTTGTGTTATCC | | 704 |

*FIG. 2*

```
LDGF2  MSLRLDTTPS CNSARPLHAL QVLLLLSLLL TALASSKGQ  TKRNLAKGKG HIFYPRGKSR Q         61
LDGF1  ********** ********** **********          ********** E          ESLDSDLYAE LRCMCIKTTS  70

LDGF1  GIHPKNIQSL EVIGKGTHCN QVEVIATLKD GRKICLDPDA PRIKKIVQKK LAGDESAD  128
```

FIG. 3A

```
                               GAATT CTTGGTAAGG ACATTTCTTG CACAATTTCT   -1080

AATAGTGCAA AATTGGAAAC ACCGTGAAGG CACCAACAAG GCAAGGTTGA GTAACTATTG       -1020

TTCTTATCAC AGGACGTCAC ATGGTCATTA AGAAGAATGG GGGAAAACTA CATTAAGATG       -960
GRE
ACCTGAAAAG ATAAGGAACA CATATTTTTT GAAGGATAAA AGTCAGCTGT ATAGTGATCC       -900

ATATACAATA CTTCTATGTA TATGTGTACC TCTATGTCTT AAACGTGTCT CATTGTATAC       -840

ATATACATGT GTGCATATAA GTGCAGACAG AATTGAAAAC TAATGCAAAA TTGTTACCAG       -780

TGTTTACCAC TGAATAGTAG GAATGTGGAG AAATGATGAA GAGAAAGTTG TGTTTTATTT       -720

CAAAGACATC TGCAGCATAC GAATCTTTTG CAATAAATTA TATAATTTTT CTGTTAAATT       -660
           Pst 1
AAAAATAAAA AGAAAAATAA ATATGCTGGG TCCTACTTTT TAGGTATTCT TAGGTGGTAG       -600

AAACAAGTAG CTTCTTTTGT AATATAAAGG AGGATGAGTT TCATTTGTAG TTTCTAGATG       -540
                                                        Xba 1
AAATTACAAA AGATAATATA GATTGAAGGC AGAAAGAATC CAATAAGCTA AAATCCAAAG       -480

ACAACCTTTG ACGGTAATTG GCTCTTATTT TACTTACATG CTCCAAACCA ATCCCAATAT       -420

TTATCAACAT TCATGAAAAG AACATTTGCT TTTCTTTGGC AAGCAAAAGA TAACTTTCTC       -360

TTTCAAGGGC CACATCTTA AGCCTAAAAA CTGCAGTATA GAAAAGGCAG GGGCGTATTG       -300

TTATAAATCA TACAAAGAAA ATGCATGTAG TATTTCAGTC TAGTTCTTAC CTTCCTGAAC       -240

GGAGTTCTTA CACAGGTGTA AGGAAGATAA GTATTGAGAA GGGAGAGTGG GAATGTGAAG       -180

TGATGCACAT TAAGCAAGTT AGTAGGAATT TGACCTGTCT GGTCTTTCTC TGGGTTGGGC       -120

ATAGCTTCAA ATGCTTATGT GTGTATCACC ACAGACCCAC ACTTCCTACC TTTCCTCCTC       -60

TTCCTTCTTA CTGGCTTTGA GAAAGAGCAT ATAAATGACA TCTTCAGGGC ATGAGAAGCC       -1
+1
ACTTATCTGC AGACTGTAGG CAGCA
        Pst 1
```

*FIG. 10*

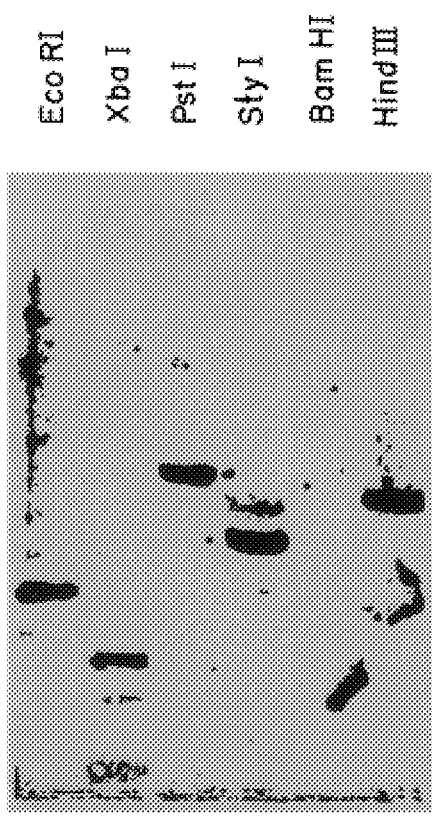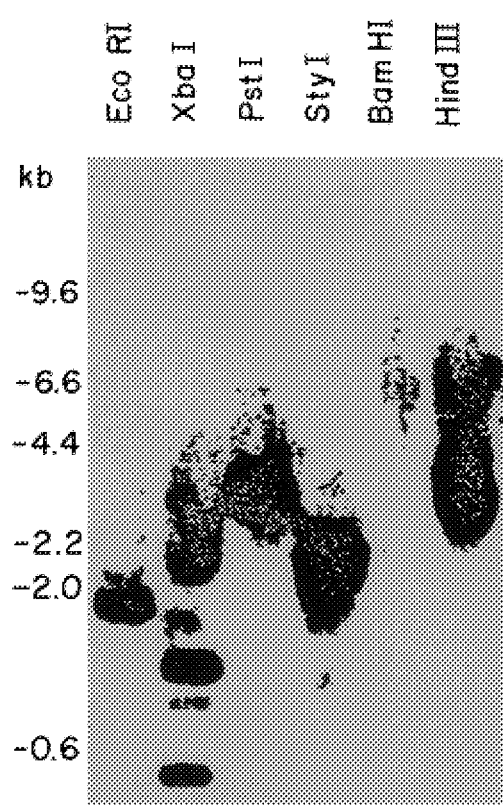
FIBROBLASTS
FIG. 11A
LYMPHOCYTES
FIG. 11B 5,849,534

DNA ENCODING LEUKOCYTE DERIVED GROWTH FACTOR-2 (LDGF-2)

RELATED APPLICATION

This application is a divisional application of Ser. No. 08/179,656 filed on Jan. 7, 1994, pending, which in turn is a continuation-in-part application of Ser. No. 08/001,177 filed on Jan. 7, 1993, now abandoned; which in turn is a continuation-in-part application of Ser. No. 07/472,377 filed on Feb. 1, 1990 now abandoned. The contents of all of the aforementioned application(s) are hereby incorporated by reference. The contents of Naoko Iida's Ph.D. dissertation also is expressly incorporated by reference.

BACKGROUND

Wound healing requires the recruitment of specialized cells to the site of the wound for the purposes of accomplishing such tasks as blood coagulation, immune responses, inflammation and tissue repair. Platelets adhere to a wound and aid in clot formation within minutes of an injury. The phagocytic cells (leukocytes and macrophages) then debride the wound, followed by the connective tissue cells (fibroblasts and smooth muscle-like cells) which proliferate and deposit extracellular matrix. The cells involved in the wound healing process produce and/or release factors which aid in the process.

Chemotaxis is the directed migration of a cell along a gradient toward the source of a chemical. A chemoattractant is a chemical which specifically stimulates chemotaxis. It is believed that it is the sequential production of cell type-specific chemoattractants which is responsible for the ordered recruitment of phagocytes, fibroblasts and endothelial cells to the wound. For example, platelet factor 4, elastin peptides and certain synthetic N-formylmethionyl peptides attract phagocytes (neutrophils and monocytes). Fibronectin and platelet-derived growth factor summon matrix producing cells and the former also stimulates endothelial cell migration.

Several biochemical events determine a cell's ability to respond to a chemoattractant, e.g. a growth factor. First, the chemoattractant molecules must be produced in a manner which allows them to reach the target cells desired for migration. Second, the target cells must be capable of detecting the chemoattractant, i.e. via receptors. Third, the binding of the chemoattractant to an appropriate receptor must in some way signal the target cell to move to the desired site, i.e. wound.

The proliferation of connective tissues at the wound is promoted by various types of growth factors. Competence factors (platelet derived growth factor, fibroblast growth factor and leukocyte derived growth factors) activate quiescent cells in the Go phase of the cell cycle enabling them to respond to progression factors. Progression factors, e.g. insulin, somatonedin A or C, alveolar macrophage-derived growth factor, stimulate the cells to enter the S-phase of the cell cycle.

Mitogens are agents which induce mitosis of a cell leading to cell growth or proliferation. Growth factors may be mitogenic, chemotactic, or both mitogenic and chemotactic, i.e. a mitoattractant. Even further, a growth factor may be a mitogen for one type of cells yet be a chemo- or mitoattractant for another type of cells. For example, platelet derived growth factor (PDGF) is both a chemoattractant and a mitogen for connective cells. Epidermal growth factor (EGF), transforming growth factors α and β, somatonedins A and C, and insulin are growth factors which are mitogenic for fibroblast cells and yet EGF is a mitoattractant for intestinal epithelial cells. The complex nature of the functions of the various growth factors make them an interesting and important field of study.

Presently, PDGF is a growth factor which has been studied extensively. PDGF has some limitations regarding its usefulness in wound repair. First, PDGF is a dimeric glycosylated protein which is difficult and expensive to produce. Second, PDGF is a relatively large molecule which also makes it more difficult to produce recombinantly or chemically than smaller molecules.

SUMMARY OF THE INVENTION

The present invention pertains to a novel protein, Leukocyte Derived Growth Factor 2 (hereinafter LDGF2) having PDGF-like activity. LDGF2 reacts with PDGF receptors and possesses mitogenic and/or chemotactic activity for various cell types, particularly connective tissue cells. LDGF2 may be used as the active ingredient in therapeutic compositions, e.g. wound healing compositions, or even further may be used as an additive to cell culture media for the purpose of stimulating cell growth.

LDGF2 may be purified from wound fluid or may be purified as a release product of activated human monocytes. The protein has a molecular weight of about 7000 daltons determined by SDS gel electrophoresis and is about 61 amino acids in length. The relatively small size of the protein is advantageous in that it is easier to produce than its larger, glycosylated PDGF counterpart. LDGF2 also is smaller than previously discovered Leukocyte Derived Growth Factor 1 (hereinafter LDGF1).

Leukocyte Derived Growth Factor 1 (hereinafter LDGF1) was previously described in copending application Ser. No. 07/472,377 filed on Feb. 1, 1990. LDGF1 and LDGF2 are structurally similar but distinct proteins in that the first 49 amino acids of each protein are the same. The last 12 amino acids of LDGF2 differ significantly from the corresponding portion of LDGF1. An interesting aspect of LDGF2 is that the first 49 amino acids represent a region that is responsible for LDGF1's activity as a connective tissue mitoattractant.

Other aspects of this invention include isolated nucleic acid, i.e. DNA, coding for LDGF2, expression vectors designed to express LDGF2, host cells transformed to express LDGF2, methods of producing LDGF2, antibodies specifically reactive with LDGF2 and therapeutic compositions and cell culture media containing LDGF2. The preferred therapeutic compositions are wound healing compositions containing a wound healing effective amount of LDGF2 and a pharmaceutically acceptable carrier.

Another important aspect of this invention pertains to the discovery that LDGF2 MRNA results from an intergenic exon exchange between the LDGF and PF4 genes and encodes two distinct polypeptides. The first being LDGF2 and the second being a fusion protein having multiple domains. The first domain of the protein is derived from a first gene (LDGF1) and the second domain is derived from a second gene (PF4) which differs from the first gene. Further, the protein exists in nature in a form that results from an intergenic exon exchange between the first and second gene that codes for a single open reading frame. The sequence of this protein is identical to that of LDGF1 beginning at the methionine residue until it fuses to the sequence in exon number 2 of the PF4 gene where the sequence is identical to that of the mature PF4 peptide. This concept is particularly important for the SIG family of C-X-C proteins because it is believed that the genes responsible for these factors or proteins are localized on an area of one chromosome. Thus, it is expected that other growth factors in this family also will be the result of intergenic exon exchanges in view of the discovery that the fusion protein is the result of an intergenic exon exchange between two genes on this chromosome.

BRIEF DESCRIPTION OF THE DRAWINGS

FIG. 2 compares the nucleotide sequences of LDGF1 (SEQ ID NO:14) and LDGF2 (SEQ ID NO:15) cDNAs. The LDGF2 cDNA contains a 19 bp insertion in the ORF introducing the premature termination codon. A unique 3' UTR in the LDGF 2 cDNA sequence is shown demonstrating that two alternative splicing events may take place for the generation of the LDGF2 transcripts.

FIG. 3A compares the amino acid sequences deduced from the cDNA sequence of the LDGF2 (SEQ ID NO:17) and LDGF1 (SEQ ID NO:16) transcripts.

FIG. 10 depicts the sequence )SEQ ID NO:18) of the nucleotide sequence of a putative promoter region of the LDGF gene.

FIG. 11 are photographs showing the genomic Southern blot analysis of the LDGF gene in two different cell types.

DETAILED DESCRIPTION

Figure 1A:
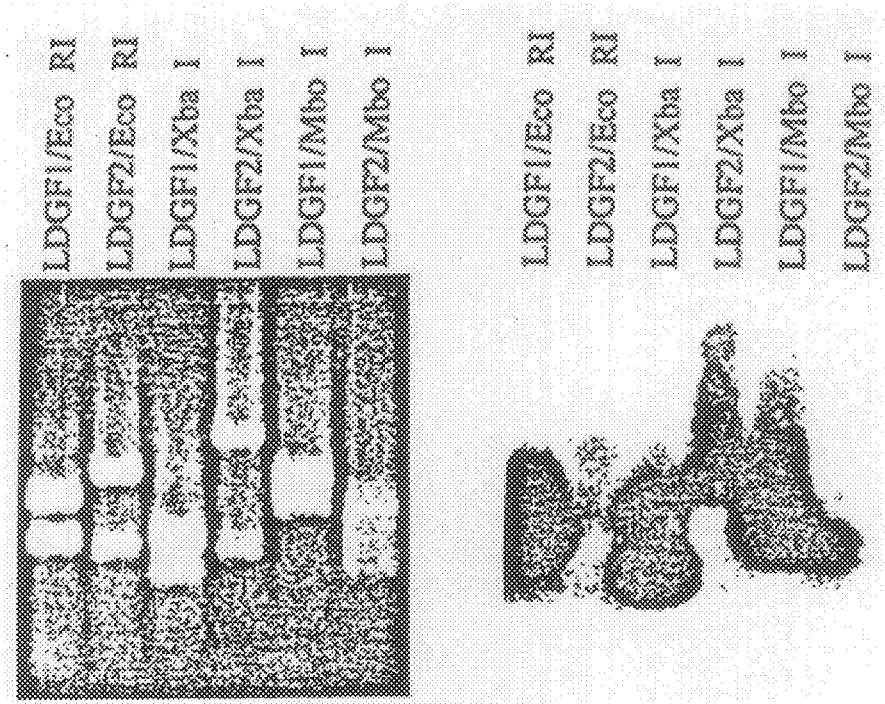
FIGS. 1A and 1B depict the analysis of LDGF1 and LDGF2 cDNA by Southern blot

The present invention pertains to a purified protein consisting essentially of LDGF2. The term purified is intended to include isolated forms of the naturally occurring or non-recombinant form of LDGF2, recombinantly produced LDGF2 and chemically synthesized LDGF2. Non-recombinant LDGF2 may be isolated from wound fluids using antibodies designed to be specifically reactive with LDGF2. Non-recombinant LDGF2 further may be isolated from culture media maintaining a culture of activated human monocytes which is discussed in detail below. The LDGF2 may be recombinantly produced by transforming a host cell to express LDGF2, e.g., inserting a nucleotide sequence coding for LDGF2 in an expression vector and transforming a host cell with the expression vector under conditions which allow expression of LDGF2 to occur. The expressed recombinant LDGF2 may be isolated using conventional techniques. The LDGF2 may be chemically synthesized using conventional techniques. The present invention provides the deduced amino acid sequence which may be used as a model for chemical synthesis.

The term "LDGF" is intended to include LDGF2, functional equivalents thereof, and antigenic fragments thereof. The term functional equivalents is intended to include proteins which differs in amino acid sequence from the LDGF2 amino acid sequence depicted in FIG. 3A but wherein the differences are of a nature which allows the modified protein to behave in the same or similar manner as LDGF2. For example, the modification may be to an amino acid which is not directly involved in LDGF2's ability to perform its intended function of reacting with the PDGF receptor. For example, the modification may be an amino acid(s) substitution, deletion or insertion. The first 49 amino acids of LDGF2 are the same as the first 49 amino acids of LDGF1. This portion of both molecules appears to be involved in the ability of both forms of the LDGF molecules to react with PDGF receptors. Modifications in the amino acid sequence of LDGF2 outside of these regions may not effect LDGF2's ability to react with the PDGF receptor and/or ability to behave as a mitogen or chemoattractant. The term functional equivalent is not intended to include LDGF1 and is intended to specifically exclude LDGF1.

The functional equivalents of LDGF2 may be prepared using any technique capable of modifying LDGF at the desired amino acid residue(s). For example, site-directed mutagenesis of DNA coding for LDGF2 may be used to produce modified DNA coding for a functionally equivalent LDGF2. Examples of other methods which may be used to introduce mutations at the nucleic acid level for coding functionally equivalents of LDGF2 include polymerase chain reaction (PCR) using oligonucleotide primers having one or more mutations (Ho et al. Gene 77:51–59 (1989)) or total synthesis of mutated genes (Hostomsky et al. *Biochem. Biophys. Res. Comm,* 161:1056–1063 (1989)).

The term antigenic fragment thereof is intended to include fragments of LDGF2 that contain a portion of LDGF2 necessary and sufficient for LDGF2 to maintain its intended function of reacting with a PDGF receptor and/or acting as a mitogen or chemoattractant. For example, the fragment including the first 49 amino acids of LDGF2 appears to contain the epitope responsible for binding of LDGF2 to a PDGF receptor because it is present in both the LDGF1 and LDGF2 molecules. This fragment is expected to share an activity which is the same or similar to LDGF2 and therefore this fragment is intended to be part of this invention. One of ordinary skill in the art would be able to take the information provided by this invention, e.g. the sequence information, and fragment LDGF2 into portions which subsequently may be screened for activity without undue experimentation especially since LDGF2 is about 61 amino acid residues long. The screening may be done using any methodology capable of detecting the activity of the fragments. For example, the blocking experiment set forth in Example 3 below may be used to screen fragments for the desired activity. These fragments are intended to be part of this invention.

This invention further pertains to a purified protein having chemotactic and/or mitogenic activity for connective tissue cells and a molecular weight of about 7000 daltons determined by SDS gel electrophoresis described in detail below. The preferred protein has both mitogenic and chemotactic activity. Mitogenic activity is the ability of the protein to induce mitosis and chemotactic activity is the ability of the protein to serve as a chemoattractant. Connective tissue cells is intended to include fibroblasts and smooth muscle-like cells. The protein may be non-recombinant, recombinant, or chemically synthesized as discussed above.

This invention even further pertains to an isolated nucleic acid having a nucleotide sequence coding for LDGF2 or equivalents thereof. The nucleic acid may be deoxyribonucleic acid, e.g. CDNA, or ribonucleic acid. The isolated nucleic acid may be isolated from a natural source or chemically synthesized using conventional techniques. For example, a probe hybridizable to the target nucleic acid sequence may be used to isolate the nucleic acid from a natural source. The nucleic acid sequence may be chemically synthesized using a solid-phase synthesis which is presently available in an automated format, e.g., a DNA synthesizer (Itakura et al., U.S. Pat. Nos. 4,598,049, 4,401, 796, 4,373,071 and Caruthers et al. U.S. Pat. No. 4,458,066. The preferred nucleic acid is cDNA having the sequence depicted in FIG. 2 (labeled LDGF2) or equivalents thereof. The term equivalents thereof is intended to include nucleotide sequences coding for functionally equivalent proteins. The modifications in the equivalent nucleic acid sequences may be made as described above.

The present invention even further pertains to expression vectors containing a nucleotide sequence coding for LDGF2, as discussed above, operably linked to at least one regulatory sequence. Operably linked is intended to mean linked in a manner which allows expression of the nucleotide sequence. Regulatory sequences are art-recognized and the regulatory sequences of this invention are selected to direct expression of LDGF2.

The term regulatory sequences includes promoters, enhancers and other expression control elements. Such regulatory sequences are art-recognized and suitable examples are described by Goeddel (*Gene Expression Technology: Methods in Enzymology* 185, Academic Press, San Diego, Calif. (1990)). It should be understood that the design of the expression vector may depend on such factors as the choice of the host cell to be transformed and/or the type of protein desired to be expressed.

This invention even further pertains to a host cell transformed to express LDGF2. The host cell may be any cell capable of expressing LDGF2. The cell may be prokaryotic or eukaryotic. Specific examples of host cells useful in this invention include *E. coli* and NIH/3T3 cells. The host cells may be transformed using any technique capable of transforming the cell with the nucleic acid in a manner which directs expression of LDGF2.

Expression in eukaryotic cells such as mammalian, yeast, or insect cells can lead to partial or complete glycosylation and/or formation of relevant inter- or intra-chain disulfide bonds of recombinant protein. Examples of vectors for expression in yeast *S cerivisae* include pYepSec1 (Baldari. et al, (1987) *Embo J.* 6:229–234), pMFa (Kurjan and Herskowitz, (1982) *Cell* 30:933–943), pJRY88 (Schultz e al, (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell*

*Biol.* 3:2156–2165) and the pVL series (Lucklow, V. A., and Summers, M. D., (1989) *Virology* 170:31–39). Generally COS cells (Gluzman, Y., (1981) *Cell* 23:175–182) are used in conjunction with such vectors as pCDM 8 (Aruffo, A. and Seed, B., (1987) *Proc. Natl. Acad. Sci. USA* 84:8573–8577) for transient amplification/expression in mammalian cells, while CHO (dhfr⁻Chinese Hamster Ovary) cells are used with vectors such as pMT2PC (Kaufman et al. (1987), *EMBO J.* 6:187–195) for stable amplification/expression in mammalian cells. Vector DNA can be introduced into mammalian cells via conventional techniques such as calcium phosphate or calcium chloride co-precipitation, DEAE-dextran-mediated transfection, or electroporation. Suitable methods for transforming host cells can be found in Sambrook et al (*Molecular Cloning: A Laboratory Manual,* 2nd Edition, Cold Spring Harbor Laboratory press (1989)), and other laboratory textbooks.

Expression in prokaryotes is most often carried out in *E. coli* with either fusion or non-fusion inducible expression vectors. Fusion vectors usually add a number of $NH_2$ terminal amino acids to the expressed target gene. These $NH_2$ terminal amino acids often are referred to as a reporter group. Such reporter groups usually serve two purposes: 1) to increase the solubility of the target recombinant protein; and 2) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase, maltose E binding protein, or protein A, respectively, to the target recombinant protein.

Inducible non-fusion expression vectors include pTrc (Amann et l, (1988) *Gene* 69:301–315) and pET 11d (Studier et al., *Gene Expression Technology: Methods in Enzymology* 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

This invention even further pertains to methods of producing LDGF2. The method includes culturing a host cell transformed with a nucleic acid vector directing expression of a nucleotide sequence coding for LDGF2. The culturing is conducted under conditions such that expression of LDGF2 occurs and the expressed LDGF2 is isolated from the culture using conventional techniques. The culture includes the host cells, media, and any other byproducts or debris. The LDGF2 may be isolated or purified culture from using techniques such as ion-exchange chromatography, gel filtration chromatography, ultrafiltration, electrophoresis and immunoaffinity purification with antibodies specific for LDGF2.

Another aspect of this invention pertains to an antibody specifically reactive with LDGF2. The antibodies of this invention may be used to isolate naturally occurring LDGF2. The antibodies may be produced using conventional techniques using the LDGF2 of this invention as an immunogen. The antibodies may be monoclonal or polyclonal. For example, a mammal, e.g. a mouse, rabbit, or goat, may be immunized with LDGF2 under conditions conducive for the animal to produce antibodies specifically reactive with LDGF2. Following immunization, anti-LDGF2, antisera may be collected and, if desired, polyclonal anti-LDGF2 antibodies isolated from the serum. Alternatively, monoclonal antibodies may be produced as follows. Antibody producing cells (lymphocytes) can be harvested from an immunized mammal and fused by standard somatic cell fusion procedures with immortalizing cells, e.g. myeloma cells, to yield hybridoma cells. The hybridoma cells can be screened immunochemically for production of monoclonal antibodies specifically reactive with LDGF2 and the monoclonal antibodies can be isolated.

The term antibody also is intended to include fragments thereof which also are specifically reactive to LDGF2. The anti-LDGF2 antibodies described above may be fragmented using conventional techniques and the fragments may be screened for utility in a manner which is the same as that used for the whole antibodies. The antibody of this invention further is intended to include bispecific and chimeric molecules having an anti-LDGF2 portion.

Another aspect of this invention pertains to therapeutic compositions containing a therapeutically effective amount of LDGF2 and a pharmaceutically acceptable carrier. The therapeutic compositions may be used to treat the conditions described in copending application Ser. No. 07/472,377 because LDGF1 and LDGF2 share similar properties and/or activities. A therapeutically effective amount is that amount sufficient to significantly reduce or alleviate symptoms associated with the particular condition or disease being treated. A preferred composition of the present invention is a wound healing composition. The wound healing composition contains a wound healing effective amount of LDGF2.

Administration of the therapeutic compositions of the present invention to an individual can be carried out using known procedures, at dosages and for periods of time effective to significantly reduce or eliminate symptoms associated with the condition or disease being treated. Effective amounts of the therapeutic compositions will vary according to the age, sex, and weight of the individual, and the ability of the LDGF2 to perform its intended function. Dosage regima may be adjusted to provide the optimum therapeutic response. For example, several divided doses may be administered daily or the dose may be proportionally reduced as indicated by the exigencies of the therapeutic situation.

The active compound (e.g., LDGF2) may be administered in a convenient manner such as by injection (subcutaneous, intravenous, etc.), oral administration, inhalation, transdermal application, or rectal administration. Depending on the route of administration, the active compound may be coated with in a material to protect the compound from the action of enzymes, acids and other natural conditions which may inactivate the compound. If the active compound is administered by injection, for example, about 1 mg–3 mg and preferably from about 20 mg–500 mg of active compound (e.g., LDGF2) per dosage unit may be administered.

To administer LDGF2 other than parenteral administration, it may be necessary to coat the protein or peptide with, or co-administer the protein or peptide with, a material to prevent its inactivation. For example, LDGF2 may be administered to an individual in an appropriate diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes (Strejan et l, (1984) *J. Neuroimmunol.* 7:27).

The active compound also may be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the LDGF2 in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., protein or peptide) plus any additional desired ingredient from a previously sterile-filtered solution thereof.

When LDGF2 is suitably protected, as described above, the protein may be orally administered, for example, with an inert diluent or an assimilable edible carrier. The protein and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit contains between from about 10 μg to about 200 mg of active compound.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with LDGF2, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieve, and (b) the limitations inherent in the art of compounding such an active compound for the treatment of sensitivity in individuals.

The LDGF2 or proteins of this invention also may be used as additives for cell culture media. A plethora of cell culture media is commercially available and LDGF2 would be desirable as an additive to these media when culturing cells to which LDGF2 has a mitogenic effect, i.e. connective tissue cells. Examples of some media to which LDGF2 may be added include minimal essential media (MEM) and Dulbecco's minimal essential media (DMEM). The LDGF2 is added to the media in a growth inducing amount, i.e. that amount which stimulates growth.

This invention even further pertains to non-naturally occurring analogues of LDGF-2 having chemotactic and/or mitogenic activity and analogues having a greater degree of homology with LDGF2 than with LDGF2, PDGF, PBP, CTAP-III or β-T6. Such analogues may be prepared using conventional techniques and screened for chemotactic and/or mitogenic activity using the methodology described herein. Analogous analogues of LDGF2 are described in copending application Ser. No. 07/472,377, the description of which also is applicable here to the extent it applies to LDGF2.

Another aspect of this invention is related to the discovery of a fusion protein that has domains coded for by nucleotide sequences derived from two different genes, i.e. the LDGF and PF4 gene. The fusion protein also can be used in wound healing compositions and in cell culture media. Thus, one aspect of this invention is an isolated protein having multiple domains. The protein has a first domain from a first gene and a second domain from a second gene which is different from the first gene. The protein is produced as a result of an intergenic exon exchanged at the nucleic acid level. This aspect of the invention is described in detail in the examples below.

EXAMPLES

The following examples further illustrate the above-described invention and should, in no way, be construed as being further limiting. The following materials and methods were used in the examples which follow. Any materials or methods not described below and mentioned in the examples are either art-recognized or described in copending application Ser. No. 07/472,377, the contents of which have been expressly incorporated by reference. All the contents of references, issued patents, pending patent applications, and published patent applications cited throughout the "Material and Methods" section and in any other part of this application are expressly incorporated by reference.

MATERIALS AND METHODS

The Human Monocyte cDNA Library Construction

Total RNA from LPS-activated monocytes was isolated by the method of Chirgwin et al. (*Biochemistry* 18:5294–5299 (1979)). Poly(A)$^+$RNA was prepared from total cytoplasmic DNA by oligo(dT) cellulose chromatography. Total RNA in 1 ml was applied to an oligo(dT) cellulose column previously equilibrated in 1× loading buffer (0.4M NaCl, 0.5% SDS, 0.01M Tris pH 7.5, and 0.001M EDTA). The column was washed with 4 ml of 1× loading buffer, and poly(A)$^+$RNA was eluted by 1 ml elution buffer (0.1M Tris (pH 7.5), 0.01M EDTA, and 1% SDS). RNA was then precipitated in 0.1× volume of 3M sodium acetate (NaOAc) pH 5.5, 2× volume of ethanol, and glycogen. The mixture was centrifuged for 10,000 rpm×15 minute at 4° C. The pellet was resuspended in 500 μl $H_2O$.

The cDNA synthesis kit was purchased from Pharmacia LKB. Approximately 5 μg poly(A)$^+$RNA in $H_2O$ was heated at 70° C. for 2 minutes. The RNA was then mixed with 1 μl DTT and First-Strand Reaction Mix (FPLCpure cloned murine reverse transcriptase, RNAguard, RNase/DNase-free BSA, oligo d(T)$_{12-18}$ primer, dATP, dCTP, dGTP, and dTTP). The first strand synthesis mix was incubated for 1 hour at 37° C. The first strand mixture was then transferred to a tube containing the Second Strand Mixture.(*E coli* RNase and *E. coli* DNA polymerase I in aqueous buffer containing dNTP's), and incubated for 1 hour at 12° C. and for 1 hour at 22° C. Then, klenow fragment of DNA polymerase (1 μl) was added and the mixture was incubated for 30 minutes at 37° C. Upon completion of the reaction, the mixture was extracted with an equal volume of phenol/$CHCl_3$ (1:1) and centrifuged for 1 minute. The upper aqueous layer was collected and purified on a Sephacryl S-300 spin column equilibrated in 1× ligation buffer (66 mM Tris-HCl (pH7.6), 1 mM spermidine, 10 mM $MgCl_2$, 15 mM DTT, and 0.2 mg/ml BSA).

Eco RI adaptors were ligated to the cDNA in a reaction mixture that contained 100 μl of the cDNA recovered from the spin column, 5 μl of the Eco RI adaptor solution, 1 μl ATP solution, and 3 μl of T4 DNA ligase. The mixture was incubated at 12° C. overnight, heated to 65° C. for 10 minutes, and placed on ice while 10 μl of the ATP solution and 1 μl of T4 polynucleotide kinase were added. This mixture was incubated at 37° C. for 30 minutes to replace the 5' terminal phosphate.

The entire cDNA synthesized was resolved on 1.0% low melting point agarose gel to size-fractionate cDNA between 400 bp and 7 kb. The cDNA was eluted from a gel slice by elutip-d column chromatography in high salt concentration. After precipitating the cDNA in ethanol, the pellet was resuspended in TE buffer. The purified cDNA was ligated into lambda gt 11 vectors (STRATAGENE) which had been digested with Eco RI and treated with alkaline phosphatase.

First, cDNA in 21 ml TE was mixed with 10 ml STE buffer and 1 μl vectors (1 μg). The cDNA and vectors were coprecipitated in NaOAc and ethanol. The pellet was then resuspended in 9 μl 1× ligation buffer (described above), and 1 μl ATP and 1 μl T4 DNA ligate were added for overnight incubation at 12° C.

The ligation reaction mixture was subjected to packaging into lambda phage particles using Gigapack Plus Packaging System (STRATAGENE). Four μl of the ligation mixture then incubated at room temperature for two hours. Finally, 0.5 ml SM buffer (0.1M NaCl, 17 mM $MgSO_4$-$7H_2O$, 50 mM Tris-HCl (pH 7.5), and 2% gelatin) and 20 ml chloroform were added to the mixture and spinned briefly to sediment debris. The supernatant was ready to be titered.

The titer of packaged mixture was measured by inoculating host bacteria strain E coli Y1088. The calculated titer of this original packaging mixture was $1 \times 10^7$ pfu, 96% of which represented recombinant bacteriophage. This cDNA library underwent one round of amplification.

Immunoscreening of the Human Monocyte cDNA Library

The original packaging mixture was subjected to immunoscreening since the initial screening of the amplified cDNA library failed. Approximately 800,000 pfu infecting E. coli Y1090, were grown on NZY plates at 42° C. for the first 2.5 hours. IPTG-coated (isopropylthio-B-D-galactoside-coated) nitrocellulose filters were placed on the plates and further incubated at 37° C. for 3.5 hours. After the filters were marked by a needle for orientation and submerged into blocking solution (1× TBS/0.5% milk) for 3×20 minutes at room temperature. The primary antibody reaction solution was prepared by mixing 210 ml 1×TBE/0.5% milk, 25 ml E coli Y1090 bacteria lysate, 420 μl anti-PDGF antibodies (1:500 dilution), and sodium azide. This solution was incubated at 4° C. for at least three hours prior to adding to the filters. Blocked nitrocellulose filters were submerged into the primary antibody reaction solution and placed on rocker platform for overnight at 4° C. Filters were then washed with 0.5% milk/1×TBE for 3×20 minutes at 4° C. and placed into the secondary antibody reaction solution (350 μl 0.5% milk/1× TBE, 350 μl secondary antibody reaction solution (350 ml 0.5% milk/1× TBE, 350 ml secondary antibodies (1:1000 dilution, alkaline phosphate-conjugated affinity purified rabbit anti-goat IgG, KPL, Gaithersburg, Mass.), and sodium azide) for two hours at 4° C. Filters were washed in 1× TBE for 20 minutes three times. To detect positive bacteriophage clones by alkaline phosphatase reaction, filters were incubated with substrates (125 mg 5-bromo-4-chloro-3-indolyl phosphate and 62.5 mg nitroblue tetrazolium) in 550 ml 0.1M Tris buffer, pH 9.0 at room temperature.

Immunopositive phage was plaque purified and LDGF phage lysate was prepared after tertiary screening to maintain homogenous population of the phage.

Preparation of anti-PDGF IgG and peptide antibodies

Human PDGF was purified from platelets using established methods (Anisowicz et al. PNAS USA 85:9645–9649 (1988); Deuel et al. J. Biol. Chem. 256:8896–8899 (1981); Heldin et al. Biochem, J. 193:907–913 (1981); and Raines et al. J. Biol Chem. 257:5154–5160 (1982)). PDGF prepared in this manner is at least 95% pure as judged by SDS-acrylamide gel electrophoresis after staining with Coomassie blue R-250 or silver stain. Thirty amino acids long synthetic peptides were purchased from Multiple Peptide Systems, San Diego, Calif. Peptide 103 consists of the first 30 amino acids at the N-terminus of LDGF1, and peptide 104 consists of amino acid residues 34–64 of LDGF1.

Antisera to purified human PDGF or synthetic peptides was prepared in goats by multiple injections of antigens in Freund's complete adjuvant followed by Freund's incomplete adjuvant. IgG was prepared from both the preimmune and immune sera using DEAE-Blue chromatography as described by the manufacturer (Bio Rad Labs., Richmond, Calif.).

Preparation of Bacterial Extract

One liter overnight bacterial culture was prepared in LB and centrifuged for 10 minutes at 3000 rpm. The pellet was washed twice with 1× TBS buffer (6.055 g Tris and 5.84 g NaCl in 1 liter $H_2O$) and resuspended in 50 ml 1× TBS buffer. The bacterial cell suspension was subjected to sonication for 4 minutes at 40% output or until lysis occurred (the suspension became viscous). The bacterial cell lysate was centrifuged for 15 minutes at 6,000 rpm, and the supernatant was transferred to a new tube where 1 ml chloroform and sodium azide were added. This bacterial extract was stored at −20° C.

Extraction of Bacteriophage Lambda DNA

Bacteriophage DNA was extracted using a 10 ml culture protocol. 0.5 ml E coli Y1090 (overnight culture with maltose and $Mg^{2+}$) was inoculated with μl of a bacteriophage stock at 37° C. for 15 minutes. Ten ml of LB media containing 10 mM $MgSO_4$ was added and incubated with shaking 9250 rpm) at 37° C. until lysis occurred. 0.1 ml $CHCl_3$ was then added and further incubated for 10 minutes. Liquid lysate was centrifuged for 10 minutes at 7,000 rpm and supernatant was treated with DNase I (final concentration of 1 μg/ml) for 30 minutes at 37° C. NaCl and PEG were added to produce final concentrations of 1.0M and 10%. After at least 90 minutes incubation on ice, the liquid lysate was centrifuged at 10,000 rpm for 15 minutes at 4° C. and the supernatant was removed. Pellets were resuspended in lambda dilution buffer (500 μl) and extracted twice with saturated phenol/$CHCl_3$ (1:1). Bacteriophage lambda DNA was precipitated with the presence of $NH_4OAc$ and ethanol. Pellets were resuspended in 50 μl TE buffer.

DNA Sequencing

Two Eco RI fragments of the LDGF1 cDNA were subcloned into M13 phage vectors and the single strand M13-LDGF1 DNA was sequenced by the use of the dideoxy chain termination method using the Sequenase Version 2.0 kit (United States Biochemical Corp., Cleveland, Ohio) and $[^{-35}S]$-dATP (dupont Co., Wilmington, Del.). Four μl (1 μg) of the ssDNA was mixed with 1 μl primer (0.5 pmol), 2 μl 5× reaction buffer (200 mM Tris-HCl (pH 7.5), 100 mM $MgCl_2$, and 250 mM NaCl), and 4 μl $H_2O$. This annealing mixture was heated at 65° C. for 2 minutes and then allowed to slowly cool to room temperature (>30 minutes). The template-primer annealing mixture was then placed on ice, and 1.0 μl 0.1M DTT, 2.0 μl undiluted labeling mix (7.5 μM dNTPs), 1.0 μl $[\alpha^{-35}S]$dATP (1000 Ci/mM), and 2.0 μl of a 1:8 dilution of Sequenase were added. This reaction mixture was incubated for 5 minutes at room temperature. Three and one half μl of the reaction mixture was transferred to 4 tube containing 2.5 μl ddGTP termination mix (80 μM dNTPs, 50 mM NaCl, and 8 μM of ddATP, ddCTP, ddGTP, or ddTTP) and incubated for 5 minutes at 37° C. The reaction was terminated by adding 4 μl stop solution (95% formamide, 20 mM EDTA, 0.05% bromophenol blue, and 0.05% xylene cyanol).

After heating the sequencing samples for 2 minutes at 95° C., both 6% and 8% acrylamide wedge gels containing 7M urea were run in 1× TBE (90 mM Tris-HCl (pH 8.2), 45 mM boric acid, and 2.5 mM EDTA) at constant voltage (1000 V) for overnight (6%) or 7 hours (8%). The gel was fixed in a 10% glacial acetic acid/10% methanol solution for 30 minutes and vacuum dried onto 3 MM Whatman chromatography paper for 2 hours at 80° C. The gel was exposed to Kodak XAR X-ray film at room temperature for at least 12 hours before the autoradiograph was obtained.

Northern Blot Analysis

Total RNA was isolated from monolayer culture cells by the method of Chomczynski and Sacchi (*Anal. Biochem.* 162:156–159 (1987)). Twenty μg total RNA was resolved in formaldehyde-1% agarose gel, and checked by ethidium bromide staining of 18S and 28S rRNA. The total RNA was transferred to nitrocellulose by capillary reaction with 20× SSC for 3 hours and the nitrocellulose was air dried and baked for 2 hours at 80° C.

Hybridization was performed overnight at 43° C. adding $1 \times 10^6$ CPM per ml of [$^{32}$P]-labeled cDNA probe synthesized using a random primer labeling kit (Boehringer Mannheim Biochemicals, Indianapolis, IN) in hybridization solution (5× NPE, 2× Denhardt's solution, 0.1% SDS, 100 μg/ml tRNA, 100 μg/ml salmon sperm DNA, and 5 μg/ml poly A RNA. The membrane was washed twice in 2× SSC/0.1% SDS for 15 minutes at room temperature and one with 0.1× SSC/0.1% SDS for 30 minutes at 43° C., then autoradiographed at −70° C. on Kodak X-OMAT 2 film for at least 3 days.

Southern Blot Analysis

The cDNA fragments from the bacteriophage lambda DNA were resolved on agarose gel (agarose low EEO electrophoretic grade, Boehringer Mannheim Biochem.) with the presence of ethidium bromide for visualization of the DNA. The agarose gel was treated in denaturation solution (0.2M NaOH and 1.5 NaCl) for 15 minutes followed by neutralization solution (1.0M Tris (pH 7.4) and 1.5M NaCl) for 45 minutes. The denatured DNA was then transferred to the nitrocellulose filters by capillary elution, and crosslinked using UV Stratalinker (STRATAGENE).

The Expression of cDNA in Bacteria and Eukaryotes

The bacterial expression of LDGF cDNA was carried out using the pET vector system developed by Studier (*Methods of Enzymology* 185:60–89 (1990)). The open reading frame of LDGF1 cDNA was PCR-amplified using primers specifically designed to add Nde 1 (5' end) and Bam HI (3' end) sites (Saiki et al., *Science* 239:487–491 (1988) (See Table 1). An amplified fragment was force-cloned into the pET3a vector under T7 RNA polymerase promoter. The pET3a-MDGF was transformed into BL21(DE3) *E. coli* strain which contained a T7 RNA polymerase gene. Bacterial cultures were grown in ZBM9 media, and at an $OD_{600}=0.7$ IPTG was added to 0.4 mM and incubated further. Twenty μl of total bacterial cultures were examined for the presence of recombinant molecules by Western blot analysis at various time points.

The eukaryotic expression of LDGF1 cDNA was facilitated by employing the human heat shock 70 promoter expression vector system. The entire LDGF1 cDNA with Hind III linker attached, was subcloned into Hind III site downstream of Hsp70 promoter in both sense and antisense orientation. The pHSP70-LDGF1 construct vector was transfected to NIH/3T3 cells along with pSVneo with the calcium phosphate transfection method. Clones were selected for G418 resistance to establish cell lines. One of the cell lines obtained was assayed for the production of LDGF1 after heat-shock (induction at 39° C.) and non heat-shock (control at 37° C.). The media from both heat-shock and non heat-shock was assayed for a biological activity and the presence of the recombinant peptide by Western blot analysis using the anti-PDGF IgG.

Western Blot Analysis

Protein samples were electrophoresed on polyacrylamide gels (15%) containing SDS (0.1%) using the method of Laemmli t (London) 227:680–685 (1970)). Fifteen percent acrylamide gels were prepared by mixing 0.375M Tris-Cl, pH 8.8, 15% Protogel (30% (w/v) acrylamide an 0.8% (w/v) bisacrylamide stock solution, National Diagnostics, Manville, N.J.), 0.1% SDS, 1.25% ammonium persulfate, and 0.05% TEMED (N,N',N'-Tetra-methylethylenediamine, Bio Rad Labs., Richmond, Calif.). The mixture was poured into gel apparatus and polymerized for one hour. The stacking gel mixture was prepared by combining 0.125M Tris-Cl, pH 6.8, 4.02% protogel, 0.1% SDS, 0.05% ammonium persulfate, and 0.05% TEMED), poured onto bottom gels, and polymerized for one hour with combs properly placed. After samples were boiled for 10 minutes in 1× sample buffer (described above) and applied to each well, the electrophoresis was carried out for one hour at 150 V in 1× running buffer (0.025M Tris-Cl, pH 8.3, 0.192M Glycine, and 0.1% SDS). Then, proteins on 15% acrylamide gels were electroblotted onto nitrocellulose filters (Schleicher and Schuell, Keene, N.H.) using a LKB Bromma 2117 multiphore II electrophoresis unit. First, gels were equilibrated in 1× transblotting buffer (29.3 g Glycine, 58.1 g Tris, and 3.75 g SDS up to 1 liter with $H_2O$). On the apparatus, 4 layers of 3MM papers, a nitrocellulose paper, a gel, and 4 additional layers of 3MM papers were placed in order, and a constant current of 70 mA/gel was applied for 2 hours. The filters were then subjected to antibody-reaction analysis.

Nonspecific antibody binding was blocked by incubating membranes with TBS (50 MM Tris-HCl (pH 7.4), 100 mM NaCl) containing 2% nonfat dry milk at room temperature for 30 minutes. When bacterial protein samples were analyzed, bacterial extract (10% v/v) from *E. coli* BL21 (DE3) was mixed with the blocking solution for 2 hours at 4° C. prior to incubation with membranes. After preincubation, the solution was removed and antibodies (15 mg/ml) was added in TBS/2% milk with 1 μg/ml sodium azide reaction mixture for overnight incubation. The membranes were then washed three times in 1× TBS/0.5% milk for 10 minutes each and incubated with alkaline phosphatase-conjugated affinity purified rabbit anti-goat IgG (KPL, Gaithersburg, Mass.) at a 1:1000 dilution in 1× TBS/0.5% milk solution for an hour at room temperature. The filters were then washed three times with 1× TBS/0.5% milk for 10 minutes each, and the blot was developed using an alkaline phosphatase substrate solution (0.1M Tris-HCl (pH 9.0), 0.25 μg/ml nitro blue tetrazolium, and 0.5 1μg/ml 5-bromo-4-chloro-3-indolyl phosphate).

Anti-PDGF IgG Conjugated Affinity Chromatography

The goat anti-PDGF IgG was dialyzed against 0.1M Hepes, pH 7.4 at 4° C. for overnight to remove glycine using a dialysis tube No. 2 (SPECTRA/POR molecularporous membrane tubing, Spectrum Medical Industries, Inc., Los Angeles, Calif.). The Affi-Gel 10 gel was purchased from Bio Rad Labs., Richmond, Calif. and washed three times with deionized water prior to use. The dialyzed goat anti-PDGF IgG was mixed with Affi-Gel 10 and incubated at 4° C. for several hours on the rocker. The anti-PDGF IgG conjugated Affi-Gel 10 was then washed several times with 0.1M Hepes, pH 7.4 and finally suspended in 0.1M Hepes at the ratio of 1:1 (v/v).

Isolation of Blood Monocytes

Human peripheral blood monocytes were isolated from buffy coats purchased from Southwest Blood Bank, Tampa, Fla. Blood monocytes were purified by centrifugation through a Hypaque-Ficoli gradient. Prior to use, 10 × PBS buffer, pH 7.4 (120 mM NaCl, 2.7 mM KCl, in 10 mM phosphate buffer, phosphate buffered saline Sigma Diagnostics, St. Louis, Mo.), $H_2O$, and Histopaque Sigma Diagnostics Histopaque 1077, Sigma Chem. Co., St. Louis, Mo.) were equilibrated at room temperature. One unit of buffy coats was diluted with approximately 30 ml 1× PBS buffer, and 20 ml of buffy coat/PBS was layered over a 20 ml Hypaque solution and centrifuged for 30 minutes at 1600 rpm. The mononuclear and granulocyte layers were removed by aspiration with a plastic pasteur pipet and the cells were diluted with DMEM containing 10% FCD. The cells were allowed to attach in T75 flasks for 2 hours at a density of $10^6$ cells/ml at 37° C. in an atmosphere of 90% air and 10% $CO_2$. Then, the medium was changed to eliminate any nonadherent cells such as red blood cells, lymphocytes, and platelets. The adherent cells (monocytes) were incubated finally in DMEM containing 2 mg/mi BSA (bovine albumin fraction V, SIGMA Chem. Co., St. Louis, Mo.) for activation by adding LPS at the final concentration of 2 μg/ml (lipopolysaccharide from *E. coli* 0111 B4 phenol extract, SIGMA Chem. Co.) After the activation, the cultured media was subjected to Affi-Gel chromatography and cells were harvested and lysed by an acetic acid method.

Preparation of Cell Extract by an Acetic Acid Method

After cultured media was removed, cells were washed twice with ice cold 1× PBS buffer. The adherent cells were scraped in. 10 ml of 1× PBS buffer and centrifuged for 5 minutes at 2000 rpm. The pellet was resuspended in 1 ml 1× PBS buffer and transferred to an eppendorf tube and centrifuged for 2 minutes at 10,000 rpm. The supernatant was discarded and 200 μl acetic acid solution (1M acetic acid and 100 mM PMSF (phenilmethylsulfonyl fluoride, SIGMA Chem. Co.) was added to resuspend the cell pellet. The cells in 1M acetic acid were incubated on ice for 15 minutes and centrifuged for 10 minutes at 14,000 rpm. The supernatant containing cell extracts were transferred to a new eppendorf tube: Typically 100 μl was lyophilized completely and resuspended in 1× sample buffer (0.0625M Tris-Cl, pH 6.8,2% SDS, and 20% glycerol) for Western blot analysis or resuspended in DMEM for biological assays.

Biological Assays

Chemotactic activity was determined in the Boyden chamber assay with NIH/3T3 cells as previously described (Grotendorst et al. *Methods Enzymol.* 146:144–152 (1987)). Confluent cultures of cells were detached from tissue culture flasks by brief trypsinization and resuspended in DMEM media with 2 mg/ml BSA. Polycarbonate filters (8 μm pores, Nucleopore, Cabin John, Md.) were coated with Type I collagen prior to the assay. The chambers are incubated for 4 hours at 37° C. in a humidified atmosphere of 90% air and 10% $CO_2$. The filters were then transferred for staining with Dif Quick stain kit Baxter, Miami, Fla.). And the chemotactic response was quantified by extracting the stain from the nuclei of cells that had migrated to the lower surface of the filters, and by measuring the absorbance at OD=600.

Screening of the Human Activated Nonocyte cDNA Library with Nucleic Acid Hybridization The original packaged mixture of the human monocyte cDNA library was screened by hybridization with a [$^{32}$P]-labeled LDGF1 cDNA as a probe. The titer of the original packaged mixture was estimated to be $5.7 \times 10^6$ pfu/500 kit (Boehringer Mannheim Biochemicals). The labeling mixture was run once through a G-50 sephadex column to separate labeled DNA from unincorporated nucleotides (Quick Spin column for radiolabeled DNA purification, Boehringer Mannheim Biochemicals).

Using *E.coli* Y1090 as a host stain, approximately 200,000 plaques were grown on NZY plates and lifted onto nitrocellulose filters (Schleicher and Schuell). The nitrocellulose filters were immediately treated in denaturation solution (0.1M NaOH, 1.5M NaCl) for 2 minutes, neutralization solution (0.2M Tris (pH 7.4), 1.5M NaCl) for 5 minutes, and 2× SSC for 2 minutes. The filters were then air dried and baked at 80° C. in vacuum for 2 hours. Nucleic acid hybridization was carried out overnight in 1× SET solution (0.6M NaCl, 0.02M EDTA (disodium), 0.2M Tris, 0.5% SDS, and 0.1% Sodium pyrophosphate) with a probe at $1 \times 10^6$ cpm/ml solution at 65° C. The filters were washed twice in 2× SSC/0.1% SDS for 15 minutes at room temperature, once in 1× SSC/0.1% SDS for 30 minutes at 65° C., and once in 0.1× SSC/0.1% SDS for 10 minutes at 65° C. The filters were then briefly dried on 3 MM paper and exposed to X-ray films overnight (Kodak diagnostic film X-OMAT).

Positive plaques were isolated and suspended in 1 ml SM buffer with $CHCL_3$. After tertiary screening, bacteriophage stocks were prepared from single plaques.

PCR Amplification of cDNA Fragments from Bacteriophage Lambda DNA

Modified lambda primers used are shown in Table 1 below. Polymerase chain reaction mixture was prepared in 100 μl volume containing 10 μl 10× raction buffer, 16 μl dNTP mix (1.25 mM each), 0.72 μl lambda primer A (138 μl), 1.04 μl lambda primer B (96 μM), Taq DNA polymerase 0.5 1μl, and Lambda gt11 template DNA (GeneAmp DNA Amplification Reagent Kit with AmpliTaq DNA polymerase, Perkin Elmer Cetus). The polymerase chain reaction was typically carried out as follows: the initial melting at 94° C. for 1 minute, annealing at 40° C. for 1 minute, polymerization at 72° C. for 2 minutes, then melting at 94° C. for 30 seconds, annealing at 55° C. for 30 seconds, and polymerization at 72° C. for 1 minute repeating 35 cycles using a gene amplification thermal cycler PTC-100 (MJ Research, Inc.).

Isolation of the Partial LDGF Gene by Polymerase Chain Reactions of Human Genomic DNA A partial LDGF gene segment was amplified by polymerase chain reaction with entire genomic DNA as a template. The reaction mixture was prepared as described above except 2 μg of total genomic DNA was added for a template DNA with primers designated for the open reading frame amplification (see Table 1).

Message Amplification Phenotyping

First strand DNA was synthesized at 37° C. for 1 hour in a final volume of 10 μl with 1.0 μl oligo-dT primers, 4.5 ml RNA in $H_2O$, 2.0 μl 5× buffer (250 mM Tris-Cl, pH 8.3, 375 mM dithiothreitol, and 15 mM $MgCl_2$), 0.5 μl RNAsin, 1.0 μl dNTP (DATP, dCTP, dGTP, dTTP mix, 10 mM each), 1.0 μl Maloney murine leukemia virus (MMLV) reverse transcriptase. Eight-five μl of PCR mix was added to 5 μl of first-strand cDNA. PCR mix contains 58.5 μl sterile water, 10 μl 10× reaction buffer (500 mM KCl, 100 mM Tris-Cl, pH 8.3, 15 mM $MgCl_2$, and 0.1% gelatin), 16 μl dNTP mix (each at 1.25 mM), and 0.5 μl (2.5 units) of the Thermus aquaticus thermostable DNA polymerase (Cetus-Perkin Elmer, Emeryville, Calif.). Five μl of each primer was added to amplify a specific segment of either LDGF2 of LDGF1 cDNA (see Table 1). The mixture was subjected to PCR amplification with the initial melting at 94° C. for 5 minutes, annealing at 37° C. for 2 minutes, and polymerization at 72°

C. for 2 minutes followed by 35 cycles of denaturation at 94° C. for 30 seconds, annealing at 55° C. for 30 seconds, and polymerization at 72° C. for 1 minute. Each sample was analyzed by 2.0% agarose gel electrophoresis, Southern blotting, and hybridization with specific cDNA probes.

Preparation of Genomic DNA from Eukaryotic Cells

Up to $10^9$ eukaryotic cells were centrifuged for 5 minutes at 2500 rpm and the medium was decanted. The pellet was washed twice with 1× PBS buffer and suspended with 10 volumes of proteinase K solution (10 mM Tris, pH 7.4, 10 mM EDTA, 150 mM NaCl, 0.4% SDS, and 1 mg/ml proteinase K). After incubation at 65° C. for 15 minutes, cells in proteinase K solution was shaken gently overnight at 37° C. The solution was extracted twice with an equal volume of 1:1 phenol:chloroform. The upper aqueous phase was transferred to a new tube, and mixed with 1/10th of 1 volume of 3M sodium acetate and 2.5 volumes of ethanol to precipitate DNA. The genomic DNA was precipitated by centrifugation for 10 minutes at 12,000 rpm. The pellet was washed with 80% ethanol and air-dried briefly. The DNA pellet was then dissolved in 4.5 ml TE buffer. Twenty five μl of 10 mg/ml RNase A (DNase free) was added and incubated for 30 minutes at 37° C. Five hundred μl of 3M sodium acetate was added and the DNA/NaOAc/TE solution was extracted with 5 ml 1:1 phenol:chloroform. After the centrifugation for 10 minutes at 10,000 rpm, the upper aqueous phase was transferred to a new tube and genomic DNA was precipitated by adding 12.5 ml of ethanol. Genomic DNA was precipitated by centrifugation for 10 minutes at 12,000 rpm, washed with 80% ethanol, and air-dry briefly. The DNA pellet was resuspended in TE buffer and the concentration was estimated by measuring O.D. at 260 nm.

Genomic Southern Blot Analysis

Approximately 10 μg of human genomic DNA was digested with various restriction endonucleases for at least two hours and purified once by phenol/CHCl$_3$ extractopm and ethanol precipitation in 2.5N NH$_4$OAc. Pellets were resuspended in 20 μl H$_2$O and resolved on 0.7% agarose at 50 V for 3 hours. Then, DNA samples were denatured, neutralized, transferred, and crosslinked to the nitrocellulose filters as described previously. The nucleic acids probes were radiolabeled with [α-$^{32}$P]-dCTP using a random primed DNA labeling kit (Boehringer Mannheim Biochemicals). The denatured probes were annealed to genomic DNA at 65° C. for overnight in 1×10$^6$ cpm/ml hybridization solution (4× NPE, 2× Denhardt's solution, 0.1% SDS, 10 μg/ml tRNA, 1% salmon sperm, and 1 μg/ml poly A RNA. Filters were washed twice with 2× SSC/0.1% SDS for 15 minutes each, once with 1× SSC/0.1% for 30 minutes at 65° C., and once with 0.1× SSC/0.1% SDS for 5 minutes at 65° C. The, filters were air dried on a 3 MM paper and exposed to x-ray films (Kodak diagnostic film X-OMAT) for at least two days.

Primer Extension

The primer extension was carried out to determine the transcription initiation site of LDGF gene. An 34-nucleotide primer was synthesized by oligonucleotide synthesis service at University of Miami (5'-ATC AAG TCT GAG GCT CAT GGT GGA GAA GGC TGAG-3') [SEQ ID NO:1].

End-labeling of oligoprimers by T4 polynucleotide kinase was carried out as follows. The reaction mixture contained 20 μl [gamma-$^{32}$P]-ATP (10 mCi/ml, NEN Research Products), 1 μl 100 μg/ml oligoprimers, 2.5 μl 10× oligokinase buffer, and 4 U T4 polynucleotide kinase (Boehringer Mannheim Corporation) and incubated at 37° C. for 30 minutes. 10× oligokinase buffer is 700 mM Tris-HCl (pH 7.5), 100 mM MgCl$_2$, 50 mM DTT, 1 mM spermidine-HCl, and 1 mM EDTA. After the incubation, the enzyme was heat deactivated at 65° C. for 5 minutes. Primers were precipitated in NH$_4$OAc and ethanol and pellets were resuspended in 25 μl of DEPC-treated H$_2$O. This was repeated two more times to eliminate unincorporated ATP. The end-labeled primers were resuspended in 100 μl 0.3M NaOAc, pH 5.2. One μl was counted by Beckman scintillation counter, LS6000 SC.

The primer extension was carried out as follows. The end-labeled primers equivalent of 1.5×10$^5$ cpm was mixed with 10 μg of total RNA. The 3M NaOAc, pH 5.2 was added to the final concentration of 0.3M, and subsequently 2.5× volume of absolute ethanol. The reaction mixture was stored at −20° C. for 30 minutes, and centrifugated 12,000 g×10 minutes at 4° C. The pellet was washed with 70% ethanol and air dried. Then, the pellet was resolved in 30 ml of hybridizaton buffer, 40 mM PIPES (pH 6.4), 1 mM EDTA (pH 8.0), 0.4M NaCl, and 80% formamide. The mixture was incubated at 85° C. for 10 minutes for denaturation, and the annealing was proceeded at 30° C. for overnight. The primer:RNA hybrids were precipitated in ethanol by incubating at 0° C. for one hour and by centrifugation 10,000 g×15 minutes at 0° C. The primer:RNA hybrids pellets was washed with 70% ethanol and resuspended in 20 μl reverse transcriptase buffer (50 mM Tris-HCl (pH 7.6), 60 mM KCl, 10 mM MgCl$_2$, 1 mM of each dNTP, 1 mM DTT, and 1 U RNasein). 50 U of murine reverse transcriptase (Boehringer Mannheim Corporation), was added to the solution to incubate at 42° C. for 1.5 hours. After reverse transcription was completed, 1 μl of 0.5M EDTA and 1 μl RNase, DNase-free (5 μg/ml, Boehringer Mannheim Corporation) were added to the reaction mixture and incubated at 37° C. for 30 minutes. Then, 150 μl of TE (pH 7.6) containing 0.1M NaCl was added to the reaction, and subsequently 200 μl phenol/CHCl3 to vortex. After centrifugation 12,000 g×5 minutes at room temperature, the upper phase was transferred to a new tube and 500 μl absolute ethanol was added. The mixture was stored at 0° C. for one hour and centrifuged 12,000 g×15 minutes at 4° C. The RNA:cDNA hybrids were dissolved in 6 μl TE and 4 μl of the sequenase stop solution (US Biochemicals Corp.) was added for further analysis by acrylamide gel electrophoresis.

Preparation of Competent Cells

Overnight cultures were prepared by inoculating frozen bacterial stocks to 5 ml LB media and 0.2 ml of the overnight culture was added to 200 ml of LB media in a one flask to incubate at 37° C. with vigorous shaking (250 rpm) until OD$_{550}$ =0.5. The bacterial culture was rapidly chilled in ice/water bath, and centrifuged for 10 minutes at 2500 rpm. The pellet was suspended well in 0.25× original volume of ice cold freshly prepared 0.1M CaCl$_2$, incubated at 0° C. for 20 minutes, and centrifuged for 10 minutes at 2500 rpm. The pellet was gently resuspended in 0.05× original volume of a freezing solution (43 ml 0.1 CaCl$_2$ and 7 ml glycerol), and aliquoted into sterile eppendorf tubes to immediately freeze at −70° C. ultracold freezer.

TABLE 1

Oligonucleotide Primers Utilized in this Invention

| | |
|---|---|
| LDGF1 ORF-5' (Nde I): | 27-mer, 5'-end of the open reading frame with Nde I site attached.<br>5'-AGG <u>CAT ATG</u> AGC CTC AGA CTT GAT ACC-3' [SEQ ID NO:2]<br>          Nde I |
| LDGF1 ORF-5' (Bam Hl): | 27-mer, 5'-end of the open reading frame with Bam Hl site attached.<br>5'-AGG <u>GGA TCC</u> AGC CTC AGA CTT GAT ACC-3' [SEQ ID NO:3]<br>          Bam Hl |
| LDGF1 ORF-3': | 27-mer, 3'-end of the open reading frame with Bam Hl site attached.<br>5'-CGC <u>GGA TCC</u> TGG CAG AAA CAG AAC AAA-3' [SEQ ID NO:4]<br>          Bam Hl |
| LDGF2 ORF-3': | 27-mer, 3'-end of the open reading frame with Bam Hl site attached.<br>5'-CTT <u>GGA TCC</u> CAG GCA CTG CAG GTC CCC-3' [SEQ ID NO:5] |
| LDGF1 UTR-5': | 18-mer, 5'end of the untranslated region of LDGF1 cDNA.<br>5'-TTT GTT CTG TTT CTG CCA-3' [SEQ ID NO:6] |
| LDGF1 UTR-3': | 18-mer, 3'end of the untranslated region of LDGF1 cDNA.<br>5'-GGG GTT GAA ACC AGG CTT-3' [SEQ ID NO:7] |
| LDGF2 UTR-5': | 18-mer, 5'end of the untranslated region of LDGF2 cDNA.<br>5'-GGG GAC CTG CAG TGC CTG-3' [SEQ ID NO:8] |
| LDGF2 UTR-3': | 18-mer, 3'end of the untranslated region of LDGF2 cDNA.<br>5'-TCA GAA GTT CTT TCA CAG-3' [SEQ ID NO:9] |
| Lambda A: | 30-mer, modified Biolabs primer #1222 to include a Sal I site.<br>5'-GGT CGA CAC CAG ACC AAC TGG TAA TGG TAG-3' [SEQ ID NO:10] |
| Lambda B: | 30-mer, modified Biolabs primer #1218 to include a Sal I site.<br>5'-GGT CGA CGG TGG CGA CGA CTC CTG GAG CCC-3' [SEQ ID NO:11] |
| LDGF IORF: | 18-mer, antisense primer at the beginning of the ORF.<br>5'-ATC AAG TCT GAG GCT CAT-3' [SEQ ID NO:12] |
| LDGF IORF PE: | 34-mer, antisense primer for primer extension analysis at the beginning of the ORF.<br>5'-ATC AAG TCT GAG GCT CAT GGT GGA GAA GGC TGA G-3' [SEQ ID NO:13] |

EXAMPLE 1

The Isolation and Sequence of a cDNA Coding for LDGF2

Figure 1B:
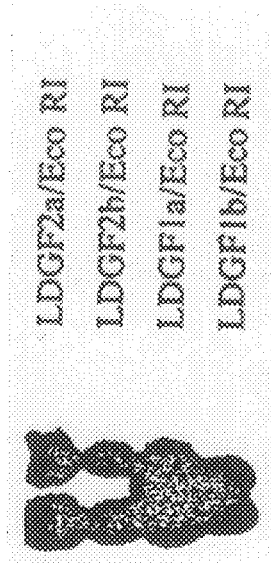

The LDGF1 cDNA and the activated human monocyte cDNA library were prepared as described previously in Ser. No. 07/472,377 filed on Feb. 1, 1990. The activated human monocyte cDNA library was screened to confirm the sequence of the LDGF1 transcript and to determine whether any other LDGF-related transcripts were present using the LDGF1 cDNA as a probe. Two recombinant phages (2AI and 3AI) strongly hybridized with the [$^{32}$P]-dCTP labeled LDGF cDNA upon screening 400,000 phage. The cDNA inserts of 2AI and 3AI were amplified using the polymerase chain reaction. Oligonucleotide primers were used which were specific for the lambda phage annealing adjacent to the cloning site. Restriction digestion analysis of the two cDNA inserts with Eco RI, Xba I and Mbo I, 3AI demonstrated that the 3AI insert exhibited the same digestion pattern as LDGF1 cDNA whereas the 2AI insert gave a different digestion pattern (FIG. 1A). Southern blot analysis demonstrated that both 3AI and 2AI hybridized with LDGF cDNA under stringent conditions (FIG. 1B).

The two inserts were subcloned in M13mpl9 for dideoxynucleotide sequence analysis. The sequence data revealed that 3AI was identical to the original LDGF1 cDNA whereas 2AI is related but distinct from 3AI in two specific details. To avoid further confusion in nomenclature, 3AI was renamed as LDGF1 and 2AI as LDGF2 where LDGF stands for leukocyte-derived growth factor.

Figure 3B:
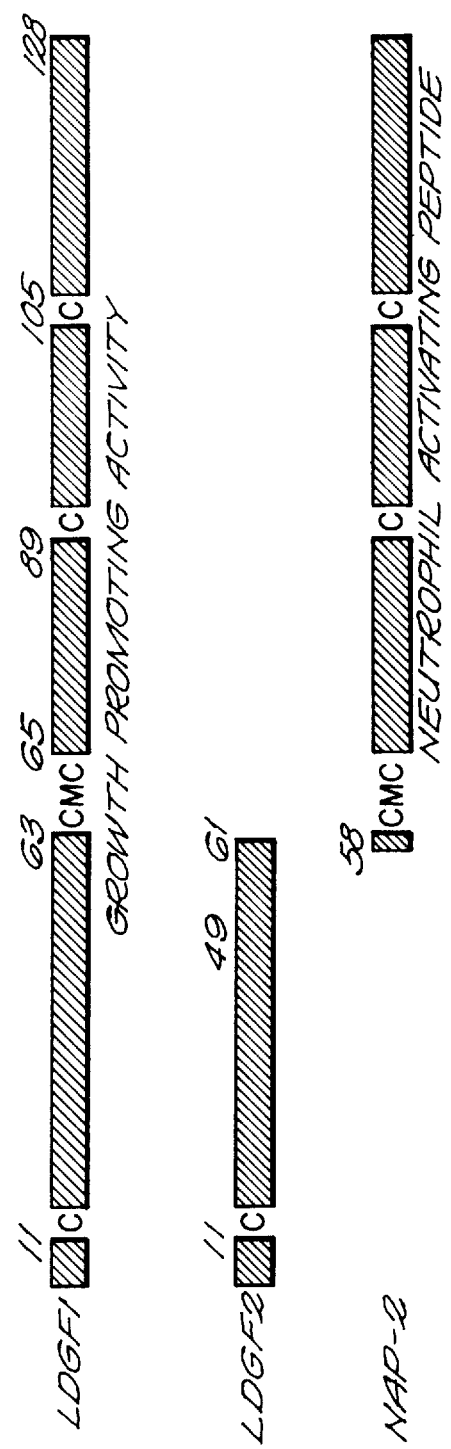
FIG. 3B is a schematic diagram showing the relationship among the LDGF gene products.

The first unique feature of the LDGF2 (2AI) sequence is a 19-base insertion in the open reading frame at position 155 (FIG. 2). The 19-base insertion results in a frame shift introducing a termination codon at position 190. This open reading frame encodes a predicted peptide of 60 amino acids (LDGF2). The first 49 amino acids at the N-terminus are identical to those of LDGF1 (MDGF) whereas the last 11 amino acids differ from LDGF1 (FIG. 3A). The second unique feature of the LDGF2 cDNA is the 3'-untranslated region (3'-UTR) which has no sequence identity with that of the LDGF1 cDNA (less than 25%, FIG. 2). The nucleotide sequence comparison of LDGF1 and LDGF2 suggests that LDGF2 MnRNA can be generated by alternative splicing of LDGF precursor transcripts. The intron-exon splice donor consensus sequence (AG/gu) was present at all the apparent splice junction sites for the 19-base insertion and LDGF2 3'-UTR.

EXAMPLE 2

Bacterial Expression of the LDGF2 cDNA

Figure 4A:
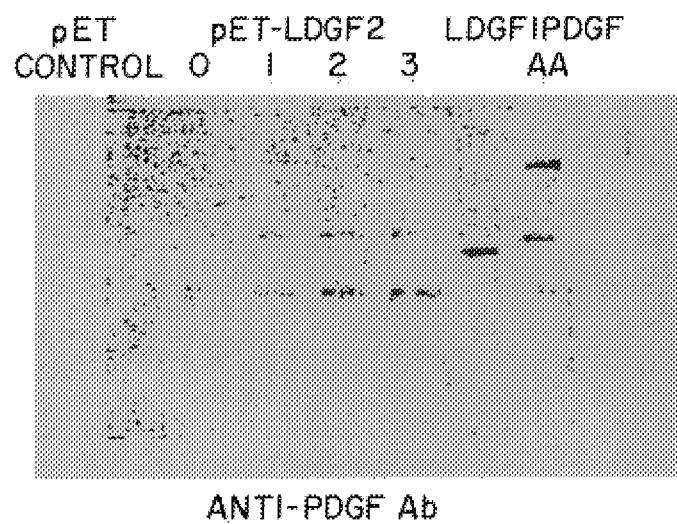
FIGS. 4A and 4B are photographs showing the Western blot analysis of the LDGF2 cDNA expressed in bacteria demonstrating the induction of the immunoreactive peptides at 7,000 daltons reacting with anti-PDGF polyclonal antibodies (A) and peptide antibodies 103 or 104 (B).

The peptide encoded in the LDGF2 cDNA was expressed in E coli using the pET system. A region of the LDGF2 cDNA was specifically amplified by PCR and subcloned into a pET3a expression vector. An E. coli BL21 (DE3) bacterial strain was transformed by either pET3a-LDGF2 or pET3A itself, and (IPTG) was added to a bacterial culture for induction when $OD_{600}$ reached 0.7. Twenty μl bacterial culture samples were taken at various times and analyzed by Western blot using anti-PDGF antibodies. The results showed the induction of an immunoreactive peptide (LDGF2) at the predicted molecular weight of approximately 7000 daltons in pET3a-LDGF2 transformed bacterial cells but not in pET3a control cells (FIG. 4A).

Figure 4B:
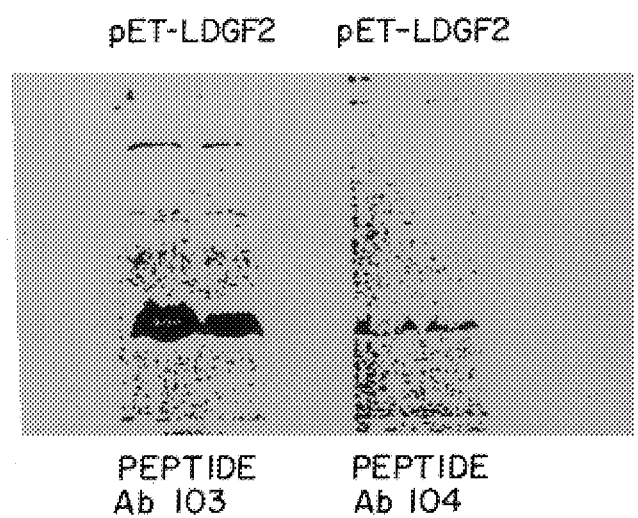
Figure 5:
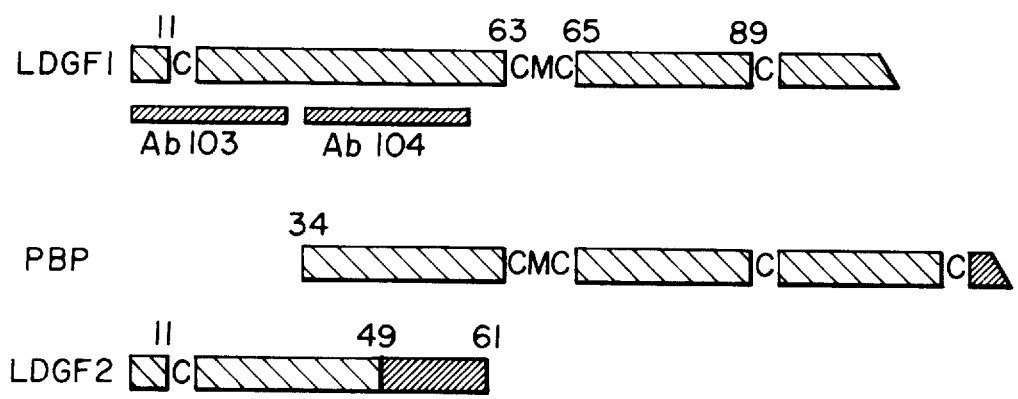
FIGS. 5, 5A, and 5B depict the immunoreactivity of LDGF1, platelet basic protein (PBP) and LDGF2 for peptide antibodies 103 or 104. The specificity of peptide antibodies 103 and 104 were examined by Western blot analysis for LDGF 1, LDGF2, and PBP.
Figure 5A:
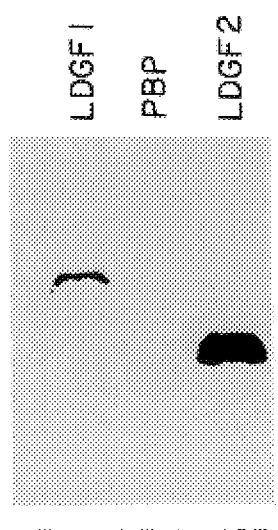
Figure 5B:

Furthermore, the synthesis of the predicted peptide was confirmed when the same bacterial culture samples were analyzed by Western blot reacting with peptide antibodies 103 (raised against a synthetic peptide consisting of the first 30 amino acids of LDGF1) (FIG. 4B). The two different peptide antibodies (Ab 103 and Ab 104, FIG. 5) are particularly useful to differentiate LDGF1, LDGF2, and other truncated forms of LDGF1 (e.g. PBP), and the high sensitivity of the two peptide antibodies was demonstrated in reducing condition by Western blot analysis (FIG. 5).

EXAMPLE 3

A Blocking Experiment Using the Recombinant LDGF1 and LDGF2

Figure 6:
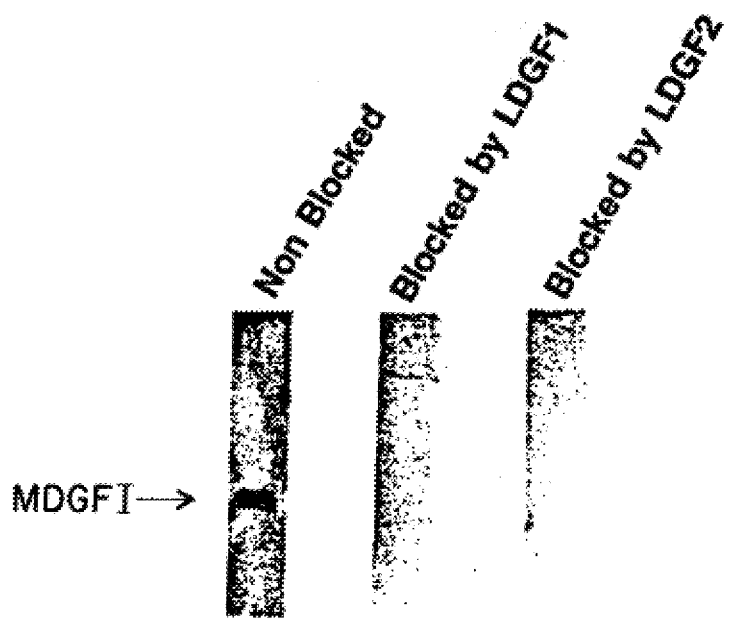
FIG. 6 is a photograph of the results of the neutralization or blocking experiment demonstrating the neutralization of non-recombinant LDGF1 by recombinant LDGF1 and LDGF2.

The recombinant LDGF's were utilized for a blocking experiment of anti-PDGF antibody immunoreactivity with the non-recombinant, purified LDGF1 molecules (FIG. 6). The non-recombinant LDGF1 was purified from the conditioned media of human LPS-activated monocyte by affinity chromatography of Affi-Gel 10 conjugated with anti-PDGF IgG. The three LDGF protein samples were examined by 15% SDS-PAGE. Western blot analysis of each sample was carried out using anti-PDGF antibodies incubated at 4° C. for two hours prior to addition to the filters under three different conditions: (1) control bacterial extract, (2) bacterial extract from LDGF 1 transformed cells, and (3) bacterial extract from LDGF 2 transformed cells. The results demonstrated that both LDGF2 and LDGF1 completely blocked the immunoreactivity of anti-PDGF antibodies with non-recombinant LDGF1 molecules (FIG. 6). These data strongly suggest that anti-PDGF antibodies are binding to the LDGF peptides within the first 49 amino acid residues of the N-terminal region.

EXAMPLE 4

Message Amplification Phenotyping (MAPPing) for Detecting LDGF1 and LDGF2 Transcripts in Activated Human Monocytes The MAPPing technique was used to provide information regarding the expression of the two LDGF transcripts in human monocytes. MAPPing was developed to analyze messenger RNAs in small numbers of cells. This technique incorporates reverse transcription of total cellular RNA to synthesize complementary DNA, followed by the polymerase chain reaction to specifically amplify DNA fragments of interest.

Two sets of oligonucleotide primers were designed for the 3'-UTRs of LDGF1 and LDGF2 where nucleotide sequence identity is less than 25% to differentiate between LDGF1 and LDGF2 transcripts. Both sets of primers were examined initially for the amplification of predicted DNA fragments in PCR using LDGF1 and LDGF2 lambda DNA as templates. Each set of primers generated the expected amplified fragment only when the appropriate template was used in the reaction. Importantly, amplified fragments of LDGF1 and LDGF2 3'-UTRs did not crosshybridize in the high stringency condition of Southern blot analysis.

Figure 7:
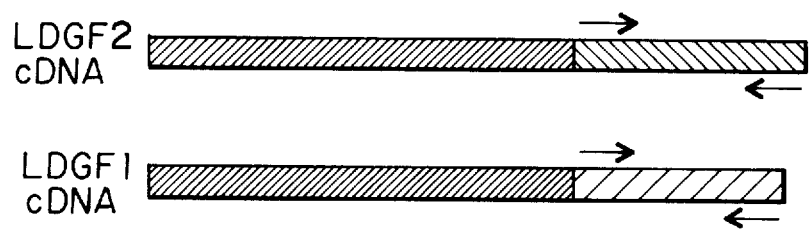
FIGS. 7, 7A and 7B depict the expression of LDGF2 transcripts analyzed using messenger amplification phenotyping (MAPPing).
Figure 7A:
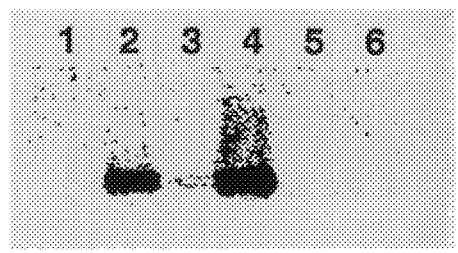
Figure 7B:
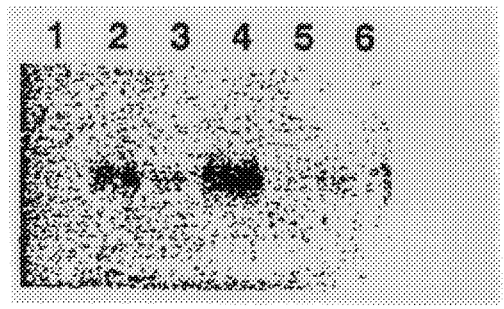
Figure 8:
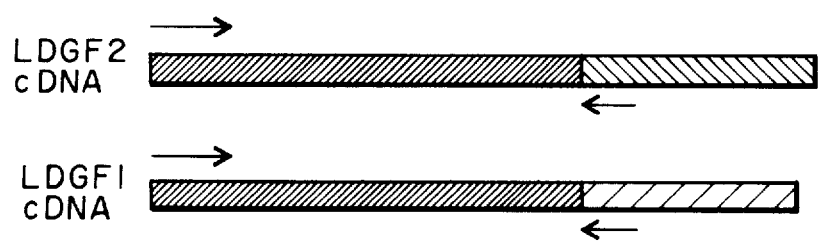
FIGS. 8, 8A and 8B depict the expression of the LDGF2 transcripts in human monocytes during activation analyzed by MAPPing.
Figure 8A:
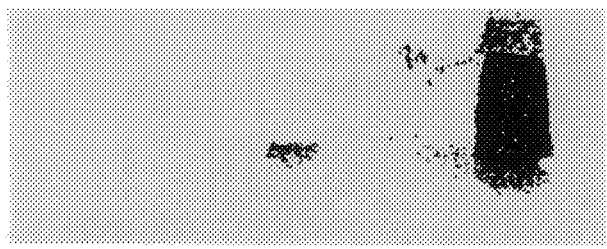
Figure 8B:
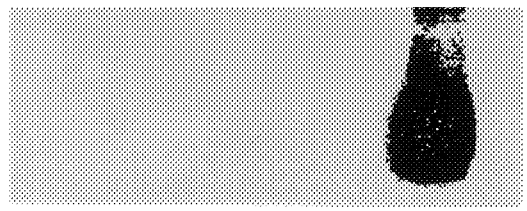

After the specificity of the two sets of 3'-UTR primers was established, MAPPing was carried out using total RNA samples prepared from: (1) non-activated human monocytes, (2) human monocytes after 5 hour LPS-activation, (3) human monocytes after 18 hour activation, (4) human activated monocytes originally used for the construction of the cDNA library, (5) human foreskin fibroblast, and (6) human smooth muscle cells. Southern blot analysis of the amplified DNA fragments revealed the presence of both LDGF1 and LDGF2 transcripts in activated human monocytes. However, no detectable amount of transcripts were observed in resting monocytes or connective tissue cells (FIGS. 7A and 7B). The MAPPing experiment was repeated using a different set of primers for detecting LDGF2 transcripts. This set of primers was previously utilized for the selective amplification of the LDGF2 ORF (see Example regarding bacterial expression of LDGF2 cDNA). The duplicate MAPPing experiment was carried out using primers utilized to amplify the LDGF1 ORF (see FIG. 8). Both reaction samples were subjected to Southern blot analysis hybridizing with the 3' UTR of the LDGF2 cDNA. The result showed the specific amplification of the LDGF2 transcripts in activated monocytes (FIG. 8), demonstrating that the common 5' sequence of LDGF1 and LDGF2 transcripts was in the same RNA transcript as the unique 3' sequence of the LDGF2 MRNA.

EXAMPLE 5

The Genomic Structure of the LDGF Gene: Evidence of the Intergenic Exon Usage Between LDGF and PF4 Genes Studies to understand the structure of the LDGF gene were intended to verify the generation of two LDGF transcripts (LDGF1 and LDGF2), in which the nucleotide sequence comparison suggested that alternative splicing of the LDGF transcripts may be the possible mechanism. It also is important to identify the promoter region so that investigations of the regulation of gene expression can be initiated. Furthermore, it is of interest from an evolutionary prospective to compare the exon/intron structure with that of other short secretory peptides in the "C-X-C" branch of the SIG family where four cysteine residues have been absolutely conserved.

One approach to the elucidation of the genomic sequence was to amplify the specific segments of the gene by polymerase chain reaction. Several pairs of oligoprimers designed for either FDGF1 or LDGF2 cDNA were examined in polymerase chain reaction with human genomic DNA as a template. The usage of oligoprimers designed to amplify the open reading frame of LDFG1 cDNA resulted in the generation of an 800 bp DNA fragment whereas only a 450 bp band was observed with LDGF1 cDNA as a template. This 800 bp band not only hybridized with an FDGF1 ORF cDNA probe but also contained an Eco RI site, indicating that this fragment was the product of the specific amplification of the LDGF gene. In order to subcloned this 800 bp fragment into a vector, it was necessary to redesign a 5' end of the primer to create a Bam HI site since the restriction enzyme Bam HI did not cleave the amplified fragment. The purified 800 bp fragment amplified from either human monocyte or fibroblast genomic DNA was then digested with Bam HI and subcloned into a M13mpl8 vector for nucleotide sequencing.

Figure 9:
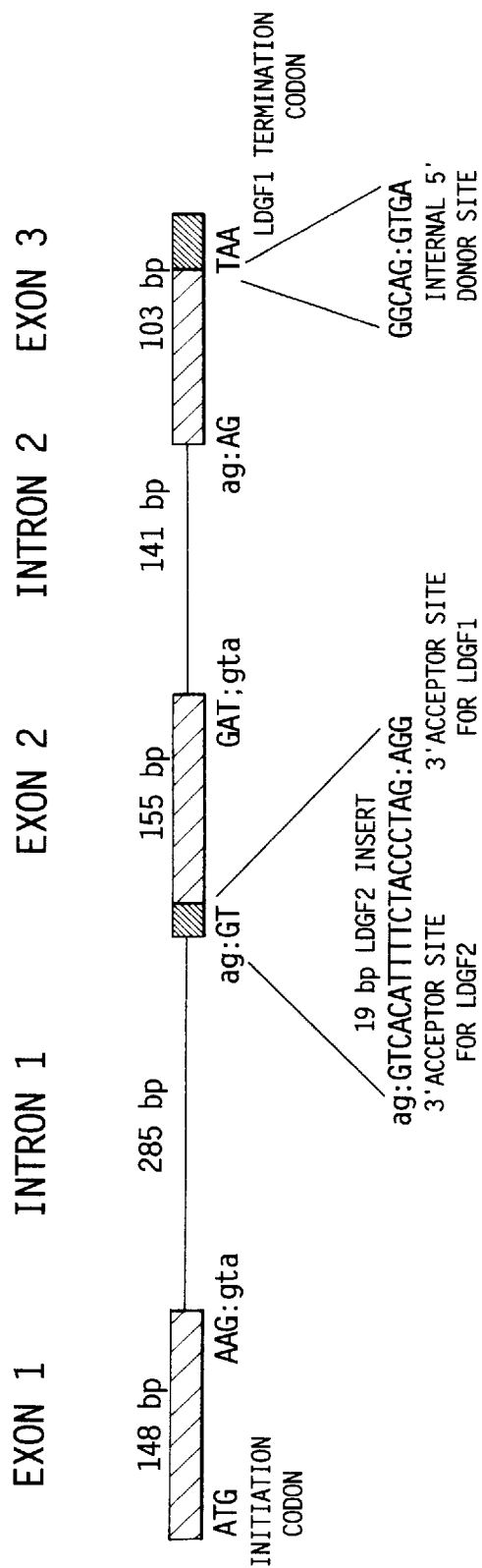
FIG. 9 is a schematic depicting the exon/intron structure of the open reading frame of the human LDGF gene.

The nucleotide sequence data of the amplified fragment revealed there were three exons and two introns within the ORF segment of the LDGF gene when compared with the LDGF1 cDNA sequence. The exon/intron splicing junctions were conserved according to consensus sequences (at 5' splice site as AG/gu and at 3' splice site ast ag/G) (FIG. 9). Surprisingly, the first 19 bp of exon 2 are identical to the 19 base insertion observed in the LDGF2 cDNA. This represents a unique alternative splicing mechanism generating LDGF1 and LDGF2 transcripts using the two 3' acceptor sites in exon 2. The splicing mechanism produces the LDGF 2 transcript by choosing the 3' acceptor site 5' to the 19 base insertion while FDGF1 transcripts are formed by using a second site that excludes the 19 base insertion. The data also indicates that another type of alternative splicing even occurs in exon 3 to differentiate the 3' untranslated regions on LDGF1 and LDGF 2 transcripts. Exon 3 contains an internal donor site which transplices to the putative exon 4 corresponding to the LDGF2 3' UTR.

EXAMPLE 6
Isolation and Sequence Analysis of a Portion of the LDGF Gene

To understand the structure and characteristics of the LDGF gene that were not resolved with polymerase chain reaction techniques, a conventional approach to the isolation of genomic clones was taken by screening a human genomic library. A human genomic library prepared from Caucasian male placenta in the Lambda FIX II vector was purchased from STRATAGENE and screened with a nucleic acid probe containing the open reading frame region of the LDGF gene described previously. Approximately one million plaques were screened and three positive plaques (1A, 2A, and 5A) were purified to homogeneity. The bacteriophage clone 1A was identical to the clone 2A when analyzed by restriction endonuclease mapping and Southern blot. The purified clone 5A did not contain any DNA fragments that hybridized with any LDGF probe.

The total bacteriophage DNA of the clone 2A was first digested with several restriction endonucleases and hybridized with a [$^{32}$P]-labeled nucleic acid probe to determine the location of the LDGF gene. Three restriction sites (Sal I, Not I, and Xba I) were present in the cloning sites of the lambda arms, and internal restriction sites (Eco RI and Xba 10 in exon 3 of the LDGF gene. The DNA digestion with these selected endonucleases followed by Southern blot analysis suggested that the gene was located in a 5.2 kb Sal I fragment next to the lambda arm, which contained a 1.9 kb Eco RI fragment that strongly hybridized with the probe and was identical to that detected in Southern blots of human genomic DNA. The Sal I (5.2 kb).and Eco RI (1.9 kb) fragments were subcloned into the pSK(+) vector for further analysis by restriction endonuclease mapping, Southern blot, and nucleotide sequencing. The data showed that the Sal I fragment spanned the part of the LDGF gene from the middle of exon 3 toward the 5' end.

Delineation of the 5' end of the LDGF gene, i.e. the putative promoter region, was begun by nucleotide sequencing. The Eco RI fragment was first subcloned into the M13 mp19 vector for single-stranded DNA sequencing using internal primers along with KS, SK, and M13 -20 primers. An antisense oligoprimer (IORF primer: inverse ORF) was designed as an 18-mer so that DNA polymerization would proceed from the beginning of the open reading frame into the promoter region. The initial nucleotide sequence data confirmed the presence of the Pst I sites in the promoter region which were elucidated by restriction enzyme mapping. Further subcloning of Pst I fragments and Xba I fragments into the M13 vector allowed the deduction of the nucleotide sequence within 1.5 kb of the putative promotor region (FIG. 10).

Figure 12:
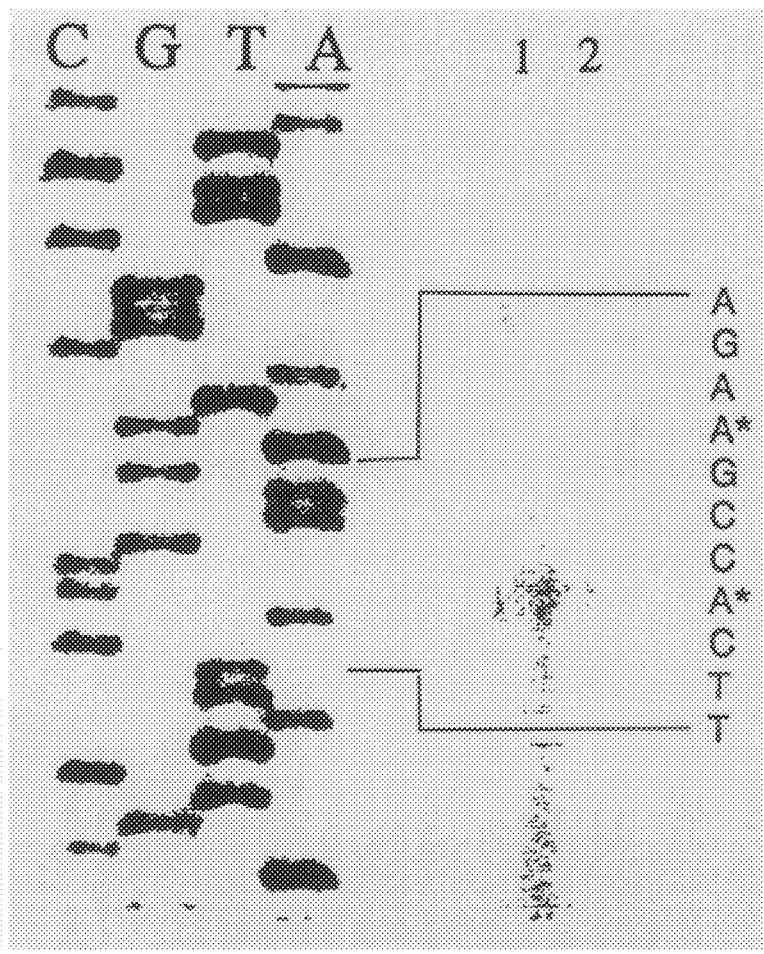
FIG. 12 depicts the primer extension analysis of the transcriptional initiation of the LDGF gene.

The transcription initiation site of LDGF gene was determined by primer extension analysis using an antisense 34-nucleotide primer. Total RNA from activated human monocytes was analyzed along with a nucleotide sequence ladder of 5% acrylamide gel (AT Biochem, Malvern Pa.). The result showed the presence of two bands consistently in two different monocyte RNA samples (FIG. 12). The intense band was observed at an adenosine residue 27-bp 3' to TATA box (TATAA), and the minor band at an adenosine 23-bp 3' to TATA box.

Figure 13:
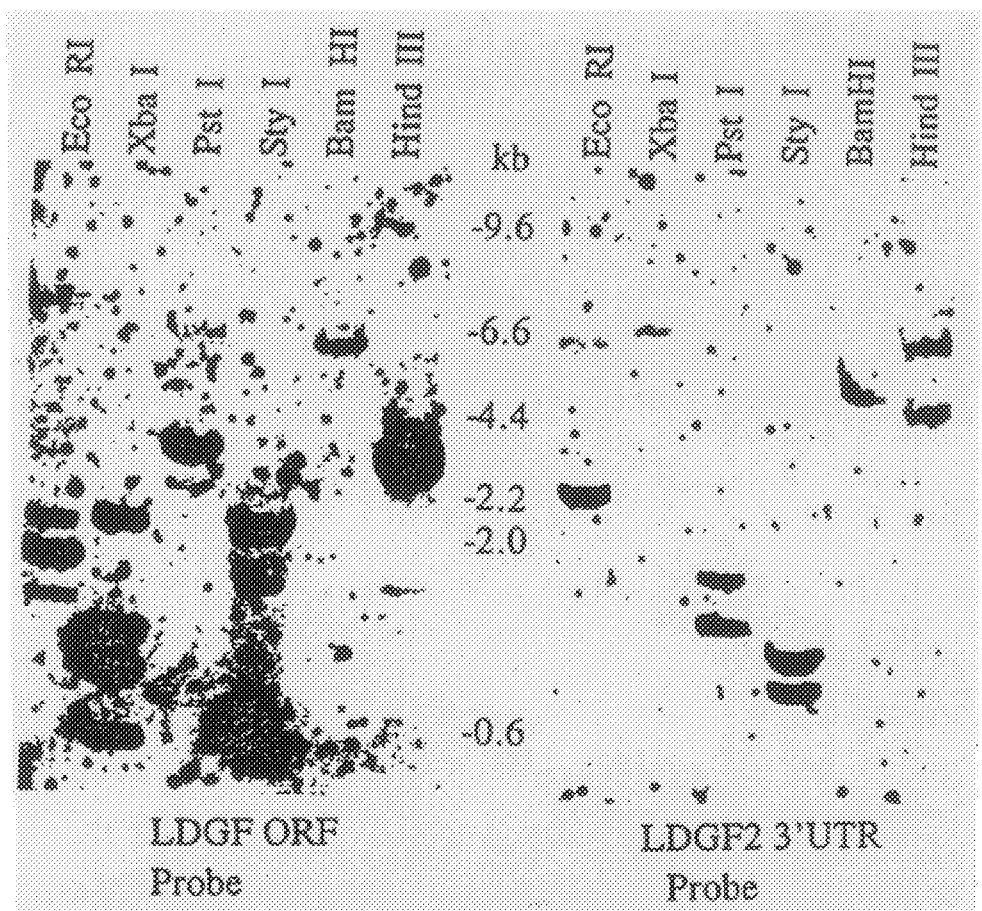
FIG. 13 are photographs of the monocyte genomic Southern blot analysis hybridized with either a LDGF ORF probe or LDGF2 3' UTR probe.
Figure 14:
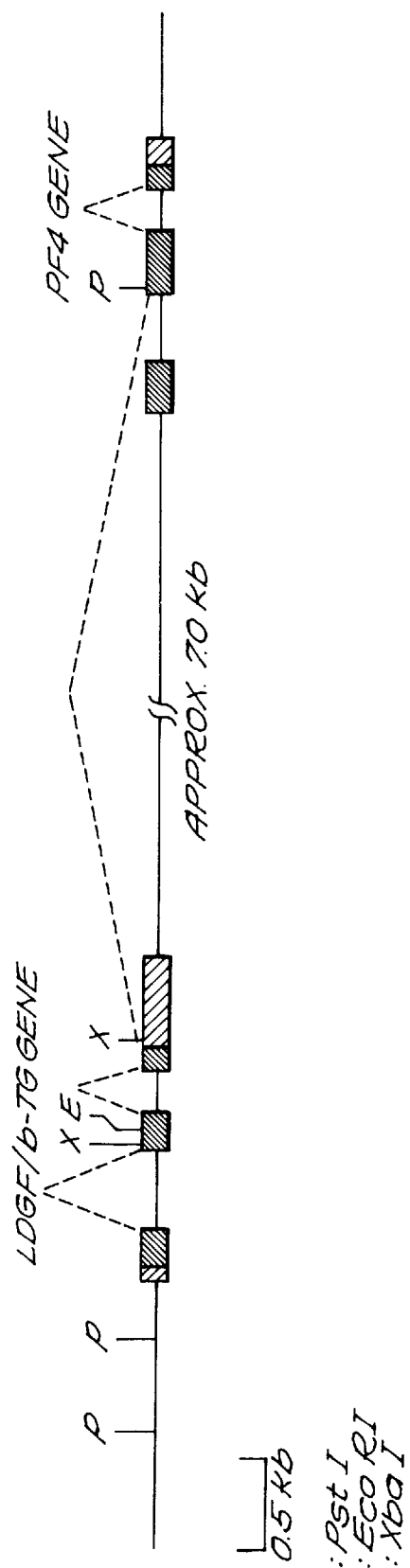
FIG. 14 is a schematic depicting the intergenic exon usage between the LDGF and PF4 genes.

Within the 1,100-bp putative promoter region sequenced, a TATA box and the CAAT box were located near the transcription start site. Examination for the presence of any known promoter consensus elements revealed only a glucocorticoid responsive element (GRE) at 1080-bp upstream from the transcription start site (FIG. 13). In addition, at approximately 900-bp upstream from the transcription initiation site an alternating purine/pyrimidine tract was present, suggesting a possible formation of Z-DNA structure which is thought to be involved in Sequence analysis of the cloned L. Sequence analysis of the cloned LDGF gene demonstrated the same exon/intron boundaries and sequence as determined in the PCR amplified fragment of human genomic DNA previously characterized. The clone did not, however, contain the putative 4th exon that was believed to be responsible for the 3' UTR region of the LDGF2 transcript. Repeated attempts to isolate other clones containing this region of human DNA were not successful. Further, PCR amplification of this region of genomic DNA suggested that it may reside in two exons.

EXAMPLE 7
Southern Blot Analysis of the LDGF Gene

Southern blot analysis of human genomic DNA was carried out. Human genomic DNA was extracted from various cell types included foreskin fibroblasts, monocytes, and lymphocytes. Approximately 10, μg of genomic DNA was digested with a variety of restriction endonucleases (Eco RI, Xba I, Pst I, Sty I, Bam HI, and Hind III), resolved on a 0.7% agarose gel, and transferred to nitrocellulose filters. Two identical genomic Southern blots were prepared to hybridize with two different nucleic acid probes: One representing the human genomic DNA containing the open reading frame of the LDGF gene amplified by PCR, and the other representing the 3' untranslated region of the LDGF2 cDNA.

The band pattern observed after hybridization with a LDGF 1 ORF probe was virtually identical among the three cell types examined, suggesting that the LDGF gene does not undergo any gene shuffling event during cell differentiation and maturation. However, this band pattern was distinct from the pattern after hybridization with a LDGF 2 3' UTR probe, which strongly indicated that the LDGF gene was relatively large and exons for the open reading frame were distant from that for the LDGF2 3' UTR. The presence of multiple bands after digestion with enzymes (Eco RI, Xba I, Pst I, Sty I, and Hind III) suggested that there may be more than one LDGF gene, or that the LDGF gene is polymorphic. The presence of multiple bands after digestion with Eco RI or Xba I was expected and confirmed since their restriction sites were predicted from the nucleotide sequence of LDGF1 and LDGF2 cDNAs.

EXAMPLE 8
The Missing Exon(s) for 3'-UTR of LDGF2 cDNA is Encoded by Exon 2 and 3 of Platelet Factor 4 Gene The nucleotide sequence of LDGF2 cDNA was compared with Genebank data base. The analysis revealed an unexpected result that 3'-UTR of LDGF2 cDNA is identical to a part of platelet factor (PF4) cDNA. PF4 is a heparin-binding protein and a major constituent of the platelet α-granules released during platelet activation. Although its exact biological function has not been determined, PF4 is thought to play a role in coagulation by neutralizing heparin-like molecules in serum and on endothelial cells. PF4 is a member of the "C-X-C" branch of the small inducible genes family. The members of this protein family are thought to be important in coagulation, inflammation, immune responses, and cell growth. Moreover, their genomic structure exhibits similar exon/intron structure, suggesting that these genes may have evolved from a common ancestral gene. The genes for all of the known members of this family are clustered in a region on human chromosome 4.

Comparison of the nucleotide sequence of PF4 gene with the 3'-UTR of LDGF2 cDNA demonstrates that this mRNA arises from the transplicing of exon 2 and exon 3 in the PF4 gene with exons 1, 2, and a portion of the 3rd exon in the LDGF/β-TG gene. The integrity of the 3' acceptor sites of exon 2 and 3 in PF4 gene are kept during this unique transplicing event. These data are the first to indicate the intergenic use of exons in any eukaryotic organism.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid having a nucleotide sequence coding for LDGF2.

2. The nucleic acid of claim 1 wherein the nucleotide sequence is a deoxyribonucleic acid sequence.

3. The isolated nucleic acid of claim 1 comprising the nucleotide sequence depicted in FIG. 2 (SEQ ID NO:15).

4. The isolated nucleic acid of claim 1 encoding LDGF2, said LDGF2 comprising the amino acid sequence depicted in FIG. 2 (SEQ ID NO:17).

5. An expression vector comprising a nucleotide sequence coding for LDGF2 as claimed in claim 4 operably linked to a regulatory sequence.

6. An isolated nucleic acid having a nucleotide sequence coding for LDGF2 said LDGF2 having immunoreactivity.

7. An expression vector comprising a nucleotide sequence coding for LDGF2 as claimed in any one of claims 1,2,3 or 6 operably linked to a regulatory sequence.

8. The expression vector of claim 7 wherein the regulatory sequence is not associated with the nucleotide sequence as it appears in nature.

9. A host cell transformed to express LDGF2, said host cell transformed with an expression vector as claimed in claim 7.

10. The host cell of claim 9 wherein the cell is prokaryotic.

11. The host cell of claim 10 wherein the cell is bacterial.

12. The host cell of claim 9 wherein the cell is eukaryotic.

13. The host cell of claim 12 wherein the cell is mammalian.

14. A host cell transformed to express LDGF2, said LDGF2 having immunoreactivity.

15. The host cell of claim 14 wherein the cell is prokaryotic.

16. The host cell of claim 15 wherein the cell is bacterial.

17. The host cell of claim 14 wherein the cell is eukaryotic.

18. The host cell of claim 17 wherein the cell is mammalian.

19. A host cell transformed to express LDGF2, said host cell transformed with an expression vector as claimed in claim 14.

20. The host cell of claim 19 wherein the cell is prokaryotic.

21. The host cell of claim 20 wherein the cell is bacterial.

22. The host cell of claim 19 wherein the cell is eukaryotic.

23. The host cell of claim 22 wherein the cell is mammalian.

24. A method of producing LDGF2 having immunoreactivity comprising:

culturing a host cell transformed with a nucleic acid vector directing expression of a nucleotide sequence coding for LDGF2 under conditions such that expression of LDGF2 occurs; and isolating the expressed LDGF2 having immunoreactivity from the culture.

\* \* \* \* \*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

ATCAAGTCTG AGGCTCATGG TGGAGAAGGC TGAG    34

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

AGGCATATGA GCCTCAGACT TGATACC    27

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AGGGGATCCA GCCTCAGACT TGATACC    27

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CGCGGATCCT GGCAGAAACA GAACAAA    27

( 2 ) INFORMATION FOR SEQ ID NO:5:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:5:

CTTGGATCCC AGGCACTGCA GGTCCCC 27

( 2 ) INFORMATION FOR SEQ ID NO:6:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:6:

TTTGTTCTGT TTCTGCCA 18

( 2 ) INFORMATION FOR SEQ ID NO:7:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:7:

GGGGTTGAAA CCAGGCTT 18

( 2 ) INFORMATION FOR SEQ ID NO:8:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:8:

GGGGACCTGC AGTGCCTG 18

( 2 ) INFORMATION FOR SEQ ID NO:9:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:9:

TCAGAAGTTC TTTCACAG 18

( 2 ) INFORMATION FOR SEQ ID NO:10:

( i ) SEQUENCE CHARACTERISTICS:
      ( A ) LENGTH: 30 base pairs
      ( B ) TYPE: nucleic acid
      ( C ) STRANDEDNESS: single (D) TOPOLOGY: linear (i i) MOLECULE TYPE: cDNA (x i) SEQUENCE DESCRIPTION: SEQ ID NO:10:

GGTCGACACC AGACCAACTG GTAATGGTAG 30

(2) INFORMATION FOR SEQ ID NO:11:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:11:

GGTCGACGGT GGCGACGACT CCTGGAGCCC 30

(2) INFORMATION FOR SEQ ID NO:12:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:12:

ATCAAGTCTG AGGCTCAT 18

(2) INFORMATION FOR SEQ ID NO:13:

(i) SEQUENCE CHARACTERISTICS:
(A) LENGTH: 34 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:13:

ATCAAGTCTG AGGCTCATGG TGGAGAAGGC TGAG 34

(2) INFORMATION FOR SEQ ID NO:14:

(i) SEQUENCE CHARACTERISTICS:
(A) LENGTH: 672 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:14:

GCAACTCACC CTCACTCAGA GGTCTTCTGG TTCTGGAAAC AACTCTAGCT CAGCCTTCTC 60

CACCATGAGC CTCAGACTTG ATACCACCCC TTCCTGTAAC AGTGCGAGAC CACTTCATGC 120

CTTGCAGGTG CTGCTGCTTC TGTCATTGCT GCTGACTGCT CTGGCTTCCT CCACCAAAGG 180

ACAAACTAAG AGAAACTTGG CGAAAGGCAA AGAGGAAAGT CTAGACAGTG ACTTGTATGC 240

TGAACTCCGC TGCATGTGTA TAAAGACAAC CTCTGGAATT CATCCCAAAA ACATCCAAAG 300

TTTGGAAGTG ATCGGGAAAG GAACCCATTG CAACCAAGTC GAAGTGATAG CCACACTGAA 360

GGATGGGAGG AAAATCTGCC TGGACCCAGA TGCTCCCAGA ATCAAGAAAA TTGTACAGAA 420

|                            |                            |                            |                            |                            |     |
| -------------------------- | -------------------------- | -------------------------- | -------------------------- | -------------------------- | --- |
| AAAATTGGCA                 | GGTGATGAAT                 | CTGCTGATTA                 | ATTTGTTCTG                 | TTTCTGCCAA  ACTTCTTTAA     | 480 |
| CTCCCAGGAA                 | GGGTAGAATT                 | TTGAAACCTT                 | GATTTTCTAG                 | AGTTCTCATT  TATTCAGGAT     | 540 |
| ACCTATTCTT                 | ACTGTATTAA                 | AATTTGGATA                 | TGTGTTTCAT                 | TCTGTCTCAA  AAATCACATT     | 600 |
| TTATTCTGAG                 | GAAGGTTGGT                 | TAAAAGATGG                 | CAGAAAGAAG                 | ATGAAAATAA  ATAAGCCTGG     | 660 |
| TTTCAACCCC                 | TC                         |                            |                            |                            | 672 |

( 2 ) INFORMATION FOR SEQ ID NO:15:

( i ) SEQUENCE CHARACTERISTICS:
        ( A ) LENGTH: 704 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

|            |            |            |            |            |           |     |
| ---------- | ---------- | ---------- | ---------- | ---------- | --------- | --- |
| TCCACCATGA | GCCTCAGACT | TGATACCACC | CCTTCCTGTA | ACAGTGCGAG | ACCACTTCAT | 60  |
| GCCTTGCAGG | TGCTGCTGCT | TCTGTCATTG | CTGCTGACTG | CTCTGGCTTC | CTCCACCAAA | 120 |
| GGACAAACTA | AGAGAAACTT | GGCGAAAGGC | AAAGGTCACA | TTTTCTACCC | TAGAGGAAAG | 180 |
| TCTAGACAGT | GACTTGTATG | CTGAACTCCG | CTGCATGTGT | ATAAAGACAA | CCTCTGGAAT | 240 |
| TCATCCCAAA | AACATCCAAA | GTTTGGAAGT | GATCGGGAAA | GGAACCCATT | GCAACCAAGT | 300 |
| CGAAGTGATA | GCCACACTGA | AGGATGGGAG | GAAAATCTGC | CTGGACCCAG | ATGCTCCCAG | 360 |
| AATCAAGAAA | ATTGTACAGA | AAAAATTGGC | AGCTGAAGCT | GAAGAAGATG | GGGACCTGCA | 420 |
| GTGCCTGTGT | GTGAAGACCA | CCTCCCAGGT | CCGTCCCAGG | CACATCACCA | GCCTGGAGGT | 480 |
| GATCAAGGCC | GGACCCCACT | GCCCCACTGC | CCAACTGATA | GCCACGCTGA | AGAATGGAAG | 540 |
| GAAAATTTGC | TTGGACCTGC | AAGCCCCGCT | GTACAAGAAA | ATAATTAAGA | AACTTTTGGA | 600 |
| GAGTTAGCTA | CTAGCTGCCT | ACGTGTGTGC | ATTTGCTATA | TAGCATACTT | CTTTTTTCCA | 660 |
| GTTTCAATCT | AACTGTGAAA | GAACTTCTGA | TATTTGTGTT | ATCC       |            | 704 |

( 2 ) INFORMATION FOR SEQ ID NO:16:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:16:

| Met<br>1 | Ser | Leu | Arg | Leu<br>5 | Asp | Thr | Thr | Pro | Cys<br>10 | Asn | Ser | Ala | Arg | Pro<br>15 |
| --- | --- | --- | --- | --- | --- | --- | --- | --- | --- | --- | --- | --- | --- | --- |
| Leu | His | Ala | Leu<br>20 | Gln | Val | Leu | Leu | Leu<br>25 | Ser | Leu | Leu | Leu<br>30 | Thr | Ala |
| Leu | Ala | Ser | Ser<br>35 | Thr | Lys | Gly | Gln | Thr<br>40 | Lys | Arg | Asn | Leu<br>45 | Ala | Lys | Gly |
| Lys | Glu<br>50 | Glu | Ser | Leu | Asp | Ser<br>55 | Asp | Leu | Tyr | Ala | Glu<br>60 | Leu | Arg | Cys | Met |
| Cys<br>65 | Ile | Lys | Thr | Thr | Ser<br>70 | Gly | Ile | His | Pro | Lys<br>75 | Asn | Ile | Gln | Ser | Leu<br>80 |
| Glu | Val | Ile | Gly | Lys<br>85 | Gly | Thr | His | Cys | Asn<br>90 | Gln | Val | Glu | Val | Ile<br>95 | Ala |
| Thr | Leu | Lys | Asp | Gly | Arg | Lys | Ile | Cys | Leu | Asp | Pro | Asp | Ala | Pro | Arg |

|            | 100                  | 105                  | 110                |
|---|---|---|---|

Ile Lys Lys Ile Val Gln Lys Lys Leu Ala Gly Asp Glu Ser Ala Asp
    115                 120                 125

( 2 ) INFORMATION FOR SEQ ID NO:17:

( i ) SEQUENCE CHARACTERISTICS:
  ( A ) LENGTH: 61 amino acids
  ( B ) TYPE: amino acid
  ( D ) TOPOLOGY: linear ( i i ) MOLECULE TYPE: peptide ( v ) FRAGMENT TYPE: internal ( x i ) SEQUENCE DESCRIPTION: SEQ ID NO:17:

Met Ser Leu Arg Leu Asp Thr Thr Pro Ser Cys Asn Ser Ala Arg Pro
1               5                   10                  15

Leu His Ala Leu Gln Val Leu Leu Leu Leu Ser Leu Leu Leu Thr Ala
            20                  25                  30

Leu Ala Ser Ser Thr Lys Gly Gln Thr Lys Arg Asn Leu Ala Lys Gly
            35                  40                  45

Lys Gly His Ile Phe Tyr Pro Arg Gly Lys Ser Arg Gln
            50                  55                  60

( 2 ) INFORMATION FOR SEQ ID NO:18:

( i ) SEQUENCE CHARACTERISTICS:
  ( A ) LENGTH: 1140 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:18:

```
GAATTCTTGG  TAAGGACATT  TCTTGCACAA  TTTCTAATAG  TGCAAAATTG  GAAACACCGT      60
GAAGGCACCA  ACAAGGCAAG  GTTGAGTAAC  TATTGTTCTT  ATCACAGGAC  GTCACATGGT     120
CATTAAGAAG  AATGGGGGAA  AACTACATTA  AGATGACCTG  AAAAGATAAG  GAACACATAT     180
TTTTTGAAGG  ATAAAAGTCA  GCTGTATAGT  GATCCATATA  CAATACTTCT  ATGTATATGT     240
GTACCTCTAT  GTCTTAAACG  TGTCTCATTG  TATACATATA  CATGTGTGCA  TATAAGTGCA     300
GACAGAATTG  AAAACTAATG  CAAAATTGTT  ACCAGTGTTT  ACCACTGAAT  AGTAGGAATG     360
TGGAGAAATG  ATGAAGAGAA  AGTTGTGTTT  TATTTCAAAG  ACATCTGCAG  CATACGAATC     420
TTTTGCAATA  AATTATATAA  TTTTTCTGTT  AAATTAAAAA  TAAAAGAAA   AATAAATATG     480
CTGGGTCCTA  CTTTTTAGGT  ATTCTTAGGT  GGTAGAAACA  AGTAGCTTCT  TTTGTAATAT     540
AAAGGAGGAT  GAGTTTCATT  TGTAGTTTCT  AGATGAAATT  ACAAAAGATA  ATATAGATTG     600
AAGGCAGAAA  GAATCCAATA  AGCTAAAATC  CAAAGACAAC  CTTTGACGGT  AATTGGCTCT     660
TATTTTACTT  ACATGCTCCA  AACCAATCCC  AATATTTATC  AACATTCATG  AAAAGAACAT     720
TTGCTTTTCT  TTGGCAAGCA  AAAGATAACT  TTCTCTTTCA  AGGGCCACAT  GTTTAAGCCT     780
AAAAACTGCA  GTATAGAAAA  GGCAGGGGCG  TATTGTTATA  AATCATACAA  AGAAAATGCA     840
TGTAGTATTT  CAGTCTAGTT  CTTACCTTCC  TGAACGGAGT  TCTTACACAG  GTGTAAGGAA     900
GATAAGTATT  GAGAAGGGAG  AGTGGGAATG  TGAAGTGATG  CACATTAAGC  AAGTTAGTAG     960
GAATTTGACC  TGTCTGGTCT  TTCTCTGGGT  TGGGCATAGC  TTCAAATGCT  TATGTGTGTA    1020
TCACCACAGA  CCCACACTTC  CTACCTTTCC  TCCTCTTCCT  TCTTACTGGC  TTTGAGAAAG    1080
```

```
AGCATATAAA  TGACATCTTC  AGGGCATGAG  AAGCCACTTA  TCTGCAGACT  GTAGGCAGCA        1140
```